United States Patent
Burns

(10) Patent No.: US 12,336,837 B2
(45) Date of Patent: Jun. 24, 2025

(54) PROVIDING A CONTINUITY OF CARE ACROSS MULTIPLE CARE SETTINGS

(71) Applicant: BRUIN BIOMETRICS, LLC, Los Angeles, CA (US)

(72) Inventor: Martin F. Burns, Los Angeles, CA (US)

(73) Assignee: BRUIN BIOMETRICS, LLC

( * ) Notice: Subject to any disclaimer, the term of this patent is extended or adjusted under 35 U.S.C. 154(b) by 0 days.

(21) Appl. No.: 16/677,623

(22) Filed: Nov. 7, 2019

(65) Prior Publication Data

US 2020/0069241 A1 Mar. 5, 2020

Related U.S. Application Data

(63) Continuation of application No. 16/193,707, filed on Nov. 16, 2018, now abandoned.
(Continued)

(51) Int. Cl.
| | |
|---|---|
| *A61B 5/00* | (2006.01) |
| *G06F 16/27* | (2019.01) |
| *G16H 10/60* | (2018.01) |
| *G16H 20/00* | (2018.01) |
| *G16H 50/30* | (2018.01) |

(52) U.S. Cl.
CPC .............. *A61B 5/445* (2013.01); *A61B 5/443* (2013.01); *A61B 5/447* (2013.01); *A61B 5/4875* (2013.01); *A61B 5/7264* (2013.01); *A61B 5/7275* (2013.01); *G06F 16/27* (2019.01); *G16H 10/60* (2018.01); *G16H 20/00* (2018.01); *G16H 50/30* (2018.01)

(58) Field of Classification Search
CPC ........ G16H 10/60; G16H 50/30; G16H 20/00; G06F 16/27; A61B 5/445; A61B 5/443; A61B 5/447; A61B 5/4875; A61B 5/7264; A61B 5/7275
See application file for complete search history.

(56) References Cited

U.S. PATENT DOCUMENTS

| | | | |
|---|---|---|---|
| 3,851,641 | A | 12/1974 | Toole et al. |
| 4,295,009 | A | 10/1981 | Weidler |

(Continued)

FOREIGN PATENT DOCUMENTS

| | | |
|---|---|---|
| AU | 2020103438 A4 | 1/2021 |
| CA | 2811609 | 11/2011 |

(Continued)

OTHER PUBLICATIONS

Christine Berggren, "Electroanalysis—Capacitive Biosensors", 2001, 13, No. 3, pp. 173-180 (Year: 2001).*

(Continued)

*Primary Examiner* — Steven G. S. Sanghera
(74) *Attorney, Agent, or Firm* — Arnold & Porter Kaye Scholer LLP

(57) ABSTRACT

The present disclosure provides methods of providing a continuity of care for a patient during transfer between care settings. The method includes the steps of deciding to transfer a patient from a first care setting to a second care setting, performing a first assessment of the patient in the first care setting, preparing a transfer record of the assessment, and transferring the transfer record with the patient to the second care setting.

25 Claims, 13 Drawing Sheets

Related U.S. Application Data

(60) Provisional application No. 62/693,810, filed on Jul. 3, 2018, provisional application No. 62/587,337, filed on Nov. 16, 2017.

(56) References Cited

U.S. PATENT DOCUMENTS

| | | | |
|---|---|---|---|
| 4,557,271 A | 12/1985 | Stoller et al. | |
| 4,857,716 A | 8/1989 | Gombrich et al. | |
| 4,860,753 A | 8/1989 | Amerena | |
| 5,001,436 A | 3/1991 | Scot | |
| 5,073,126 A | 12/1991 | Kikuchi et al. | |
| 5,152,296 A | 10/1992 | Simons | |
| 5,284,150 A | 2/1994 | Butterfield et al. | |
| 5,292,341 A | 3/1994 | Snell | |
| 5,367,789 A * | 11/1994 | Lamont | A43B 5/0415 128/892 |
| 5,815,416 A | 9/1998 | Liebmann et al. | |
| 5,904,581 A | 5/1999 | Pope et al. | |
| 6,185,452 B1 | 2/2001 | Schulman | |
| 6,204,749 B1 | 3/2001 | Ishihara | |
| 6,223,088 B1 | 4/2001 | Scharnberg et al. | |
| 6,254,435 B1 | 7/2001 | Cheong et al. | |
| 6,312,263 B1 | 11/2001 | Higuchi et al. | |
| 6,330,479 B1 | 12/2001 | Stauffer | |
| 6,368,284 B1 | 4/2002 | Bardy | |
| 6,370,426 B1 | 4/2002 | Campbell et al. | |
| 6,434,422 B1 | 8/2002 | Tomoda et al. | |
| 6,577,700 B1 | 6/2003 | Fan et al. | |
| 6,634,045 B1 * | 10/2003 | DuDonis | A47C 20/021 5/632 |
| 6,738,798 B1 * | 5/2004 | Ploetz | A61B 6/56 345/581 |
| 6,756,793 B2 * | 6/2004 | Hirono | G01R 27/2605 73/335.04 |
| 6,963,772 B2 | 11/2005 | Bloom et al. | |
| 7,079,899 B2 | 7/2006 | Petrofsky | |
| 7,291,023 B1 | 11/2007 | Still et al. | |
| 7,315,767 B2 | 1/2008 | Caduff et al. | |
| 7,402,135 B2 | 7/2008 | Leveque et al. | |
| 7,783,344 B2 | 8/2010 | Lackey et al. | |
| 8,011,041 B2 * | 9/2011 | Hann | A61B 5/447 5/652.1 |
| 8,060,315 B2 | 11/2011 | Brosette et al. | |
| 8,355,925 B2 * | 1/2013 | Rothman | G16H 15/00 705/2 |
| 8,390,583 B2 | 3/2013 | Forutanpour et al. | |
| 8,494,617 B2 | 7/2013 | Baker, Jr. et al. | |
| 8,648,707 B2 | 2/2014 | Franz et al. | |
| 8,690,785 B2 | 4/2014 | Lading | |
| 8,724,833 B1 | 5/2014 | Shain et al. | |
| 8,925,392 B2 | 1/2015 | Esposito et al. | |
| 9,028,407 B1 * | 5/2015 | Bennett-Guerrero | A61B 5/4094 600/301 |
| 9,095,305 B2 | 8/2015 | Engler et al. | |
| 9,220,455 B2 | 12/2015 | Sarrafzadeh et al. | |
| 9,271,676 B2 | 3/2016 | Alanen et al. | |
| 9,398,879 B2 | 7/2016 | Sarrafzadeh et al. | |
| 9,675,289 B2 * | 6/2017 | Heaton | G16H 40/63 |
| 9,763,596 B2 | 9/2017 | Tonar et al. | |
| 9,949,683 B2 | 4/2018 | Afentakis | |
| 9,980,673 B2 | 5/2018 | Sarrafzadeh et al. | |
| 10,085,643 B2 | 10/2018 | Bandic et al. | |
| 10,126,340 B2 | 11/2018 | Simmons | |
| 10,166,387 B2 | 1/2019 | Bergelin et al. | |
| 10,178,961 B2 | 1/2019 | Tonar et al. | |
| 10,182,740 B2 | 1/2019 | Tonar et al. | |
| 10,188,340 B2 | 1/2019 | Sarrafzadeh et al. | |
| 10,194,856 B2 | 2/2019 | Afentakis et al. | |
| 10,206,604 B2 | 2/2019 | Bergelin et al. | |
| 10,226,187 B2 | 3/2019 | Al-Ali et al. | |
| 10,278,636 B2 | 5/2019 | Wu et al. | |
| 10,285,898 B2 | 5/2019 | Douglas et al. | |
| 10,307,060 B2 | 6/2019 | Tran | |
| 10,342,482 B1 | 7/2019 | Lisy et al. | |
| 10,383,527 B2 | 8/2019 | Al-Ali | |
| 10,420,602 B2 | 9/2019 | Horton et al. | |
| 10,441,185 B2 | 10/2019 | Rogers et al. | |
| 10,448,844 B2 | 10/2019 | Al-Ali et al. | |
| 10,463,293 B2 | 11/2019 | Maharbiz et al. | |
| 10,485,447 B2 | 11/2019 | Tonar et al. | |
| 10,898,129 B2 | 1/2021 | Burns et al. | |
| 10,950,960 B2 | 3/2021 | Burns et al. | |
| 10,959,664 B2 | 3/2021 | Burns et al. | |
| 11,172,871 B2 | 11/2021 | Bly et al. | |
| 11,191,477 B2 | 12/2021 | Burns | |
| 11,253,192 B2 | 2/2022 | Sarrafzadeh et al. | |
| 11,284,810 B2 | 3/2022 | Tonar et al. | |
| 11,304,652 B2 | 4/2022 | Burns et al. | |
| 11,337,651 B2 | 5/2022 | Burns et al. | |
| 11,342,696 B2 | 5/2022 | Burns et al. | |
| 11,426,118 B2 | 8/2022 | Burns | |
| 11,471,094 B2 | 10/2022 | Burns et al. | |
| 11,534,077 B2 | 12/2022 | Tonar et al. | |
| 11,600,939 B2 | 3/2023 | Burns et al. | |
| 11,627,910 B2 | 4/2023 | Burns et al. | |
| 11,642,075 B2 | 5/2023 | Burns et al. | |
| 11,779,265 B2 | 10/2023 | Sarrafzadeh et al. | |
| 11,824,291 B2 | 11/2023 | Burns et al. | |
| 11,832,929 B2 | 12/2023 | Tonar et al. | |
| 11,980,475 B2 | 5/2024 | Burns et al. | |
| 12,097,041 B2 | 9/2024 | Burns et al. | |
| 12,132,271 B2 | 10/2024 | Burns et al. | |
| 2001/0049609 A1 | 12/2001 | Girouard et al. | |
| 2001/0051783 A1 | 12/2001 | Edwards et al. | |
| 2002/0016535 A1 | 2/2002 | Martin et al. | |
| 2002/0032485 A1 | 3/2002 | Flam et al. | |
| 2002/0070866 A1 | 6/2002 | Newham | |
| 2002/0112898 A1 | 8/2002 | Honda et al. | |
| 2002/0143262 A1 * | 10/2002 | Bardy | A61B 5/046 600/508 |
| 2003/0009244 A1 | 1/2003 | Engleson et al. | |
| 2003/0036674 A1 | 2/2003 | Bouton | |
| 2003/0036713 A1 | 2/2003 | Bouton et al. | |
| 2003/0110662 A1 | 6/2003 | Gilman et al. | |
| 2003/0116447 A1 | 6/2003 | Surridge et al. | |
| 2003/0130427 A1 | 7/2003 | Cleary et al. | |
| 2003/0139255 A1 | 7/2003 | Lina | |
| 2003/0199783 A1 | 10/2003 | Bloom et al. | |
| 2004/0041029 A1 | 3/2004 | Postman et al. | |
| 2004/0046668 A1 | 3/2004 | Smith et al. | |
| 2004/0054298 A1 | 3/2004 | Masuo et al. | |
| 2004/0080325 A1 | 4/2004 | Ogura | |
| 2004/0133092 A1 | 7/2004 | Kain | |
| 2004/0147977 A1 | 7/2004 | Petrofsky | |
| 2004/0171962 A1 | 9/2004 | Leveque et al. | |
| 2004/0176754 A1 | 9/2004 | Island et al. | |
| 2004/0236200 A1 | 11/2004 | Say et al. | |
| 2004/0254457 A1 | 12/2004 | Van Der Weide | |
| 2005/0027175 A1 | 2/2005 | Yang | |
| 2005/0049658 A1 | 3/2005 | Connors et al. | |
| 2005/0070778 A1 | 3/2005 | Lackey et al. | |
| 2005/0086072 A1 | 4/2005 | Fox, Jr. et al. | |
| 2005/0096513 A1 | 5/2005 | Ozguz et al. | |
| 2005/0177061 A1 | 8/2005 | Alanen et al. | |
| 2005/0203435 A1 | 9/2005 | Nakada | |
| 2005/0215918 A1 | 9/2005 | Frantz et al. | |
| 2005/0245795 A1 | 11/2005 | Goode et al. | |
| 2005/0251418 A1 | 11/2005 | Fox, Jr. et al. | |
| 2006/0052678 A1 | 3/2006 | Drinan et al. | |
| 2006/0058593 A1 | 3/2006 | Drinan et al. | |
| 2006/0097949 A1 | 5/2006 | Luebke et al. | |
| 2006/0206013 A1 | 9/2006 | Rothman et al. | |
| 2006/0239547 A1 | 10/2006 | Robinson et al. | |
| 2007/0043282 A1 | 2/2007 | Mannheimer et al. | |
| 2007/0051362 A1 | 3/2007 | Sullivan et al. | |
| 2007/0106172 A1 | 5/2007 | Abreu | |
| 2007/0179585 A1 | 8/2007 | Chandler et al. | |
| 2007/0185392 A1 | 8/2007 | Sherman et al. | |
| 2007/0191273 A1 | 8/2007 | Ambati et al. | |
| 2007/0213700 A1 | 9/2007 | Davison et al. | |
| 2007/0248542 A1 | 10/2007 | Kane et al. | |
| 2008/0009764 A1 | 1/2008 | Davies | |

(56) References Cited

U.S. PATENT DOCUMENTS

| | | |
|---|---|---|
| 2008/0015894 A1* | 1/2008 | Miller .................... G16H 50/20 705/2 |
| 2008/0027509 A1 | 1/2008 | Andino et al. |
| 2008/0039700 A1 | 2/2008 | Drinan et al. |
| 2008/0048680 A1 | 2/2008 | Hargreaves et al. |
| 2008/0054276 A1 | 3/2008 | Vogel et al. |
| 2008/0063363 A1 | 3/2008 | Kientz et al. |
| 2008/0166268 A1 | 7/2008 | Yamaguchi et al. |
| 2008/0259577 A1 | 10/2008 | Hu et al. |
| 2008/0278336 A1 | 11/2008 | Ortega et al. |
| 2009/0047694 A1 | 2/2009 | Shuber |
| 2009/0054752 A1 | 2/2009 | Jonnalagadda et al. |
| 2009/0076410 A1 | 3/2009 | Libbus et al. |
| 2009/0104797 A1 | 4/2009 | Tseng et al. |
| 2009/0124924 A1 | 5/2009 | Eror et al. |
| 2009/0189092 A1 | 7/2009 | Aoi et al. |
| 2009/0209830 A1 | 8/2009 | Nagle et al. |
| 2009/0285785 A1 | 11/2009 | Jimi et al. |
| 2009/0306487 A1 | 12/2009 | Crowe et al. |
| 2009/0326346 A1 | 12/2009 | Kracker et al. |
| 2010/0017182 A1 | 1/2010 | Voros et al. |
| 2010/0030167 A1 | 2/2010 | Thirstrup et al. |
| 2010/0042389 A1 | 2/2010 | Farruggia et al. |
| 2010/0073170 A1 | 3/2010 | Siejko et al. |
| 2010/0113979 A1 | 5/2010 | Sarrafzadeh et al. |
| 2010/0152551 A1 | 6/2010 | Hsu et al. |
| 2010/0268111 A1 | 10/2010 | Drinan et al. |
| 2010/0298687 A1 | 11/2010 | Yoo et al. |
| 2010/0312076 A1 | 12/2010 | Bly et al. |
| 2010/0312233 A1 | 12/2010 | Furnish et al. |
| 2010/0324455 A1 | 12/2010 | Rangel et al. |
| 2010/0324611 A1 | 12/2010 | Deming et al. |
| 2011/0015697 A1 | 1/2011 | McAdams |
| 2011/0046505 A1 | 2/2011 | Cornish et al. |
| 2011/0160548 A1 | 6/2011 | Forster |
| 2011/0175844 A1 | 7/2011 | Berggren |
| 2011/0184264 A1 | 7/2011 | Galasso et al. |
| 2011/0191122 A1* | 8/2011 | Kharraz Tavakol ... G06Q 50/22 705/3 |
| 2011/0223078 A1 | 9/2011 | Ohashi |
| 2011/0237926 A1 | 9/2011 | Jensen |
| 2011/0263950 A1 | 10/2011 | Larson et al. |
| 2011/0301441 A1 | 12/2011 | Bandic et al. |
| 2011/0313311 A1 | 12/2011 | Gaw |
| 2012/0029410 A1 | 2/2012 | Koenig et al. |
| 2012/0061257 A1 | 3/2012 | Yu et al. |
| 2012/0078088 A1 | 3/2012 | Whitestone et al. |
| 2012/0083672 A1 | 4/2012 | Cui et al. |
| 2012/0150011 A1 | 6/2012 | Besio |
| 2012/0179006 A1 | 7/2012 | Jansen et al. |
| 2012/0190989 A1 | 7/2012 | Kaiser et al. |
| 2012/0271121 A1 | 10/2012 | Della Torre et al. |
| 2013/0041235 A1 | 2/2013 | Rogers et al. |
| 2013/0072870 A1 | 3/2013 | Heppe et al. |
| 2013/0121544 A1 | 5/2013 | Sarrafzadeh et al. |
| 2013/0123587 A1 | 5/2013 | Sarrafzadeh et al. |
| 2013/0137951 A1 | 5/2013 | Chuang et al. |
| 2013/0253285 A1 | 9/2013 | Bly et al. |
| 2013/0261496 A1 | 10/2013 | Engler et al. |
| 2013/0301255 A1 | 11/2013 | Kim et al. |
| 2013/0310440 A1 | 11/2013 | Duskin et al. |
| 2013/0333094 A1 | 12/2013 | Rogers et al. |
| 2013/0338661 A1 | 12/2013 | Behnke, II |
| 2014/0121479 A1 | 5/2014 | O'Connor et al. |
| 2014/0142984 A1 | 5/2014 | Wright et al. |
| 2014/0288397 A1 | 6/2014 | Sarrafzadeh et al. |
| 2014/0200486 A1 | 7/2014 | Bechtel et al. |
| 2014/0221792 A1 | 8/2014 | Miller et al. |
| 2014/0273025 A1 | 9/2014 | Hurskainen et al. |
| 2014/0275823 A1 | 9/2014 | Lane et al. |
| 2014/0298928 A1* | 10/2014 | Duesterhoft ...... A61F 13/00051 73/865.8 |
| 2014/0316297 A1 | 10/2014 | McCaughan et al. |
| 2014/0318699 A1 | 10/2014 | Longinotti-Buitoni et al. |
| 2014/0365241 A1 | 12/2014 | Dillie et al. |
| 2015/0002168 A1 | 1/2015 | Kao et al. |
| 2015/0009168 A1 | 1/2015 | Levesque et al. |
| 2015/0094548 A1 | 4/2015 | Sabatini et al. |
| 2015/0157435 A1 | 6/2015 | Chasins et al. |
| 2015/0186607 A1* | 7/2015 | Geleijnse ............... G16H 50/20 705/2 |
| 2015/0230863 A1 | 8/2015 | Youngquist et al. |
| 2015/0343173 A1 | 12/2015 | Tobescu et al. |
| 2015/0363567 A1 | 12/2015 | Pettus |
| 2015/0366499 A1 | 12/2015 | Sarrafzadeh et al. |
| 2015/0371522 A1 | 12/2015 | Mravyan et al. |
| 2016/0015962 A1 | 1/2016 | Shokoueinejad Maragheh et al. |
| 2016/0038055 A1 | 2/2016 | Wheeler et al. |
| 2016/0058342 A1 | 3/2016 | Maiz-Aguinaga et al. |
| 2016/0072308 A1 | 3/2016 | Nyberg et al. |
| 2016/0081580 A1 | 3/2016 | Bergelin et al. |
| 2016/0100790 A1 | 4/2016 | Cantu et al. |
| 2016/0101282 A1 | 4/2016 | Bergelin et al. |
| 2016/0166438 A1 | 6/2016 | Rovaniemi |
| 2016/0174631 A1 | 6/2016 | Tong et al. |
| 2016/0174871 A1 | 6/2016 | Sarrafzadeh et al. |
| 2016/0220172 A1 | 8/2016 | Sarrafzadeh et al. |
| 2016/0270672 A1 | 9/2016 | Chen et al. |
| 2016/0270968 A1 | 9/2016 | Stanford et al. |
| 2016/0278692 A1* | 9/2016 | Larson .................. G16H 20/10 |
| 2016/0296268 A1 | 10/2016 | Gee et al. |
| 2016/0310034 A1* | 10/2016 | Tonar ..................... A61B 5/742 |
| 2016/0338591 A1* | 11/2016 | Lachenbruch ....... A61B 5/7405 |
| 2016/0374588 A1 | 12/2016 | Shariff |
| 2017/0007153 A1* | 1/2017 | Tonar .................. A61B 5/6801 |
| 2017/0014044 A1 | 1/2017 | Tonar et al. |
| 2017/0014045 A1 | 1/2017 | Tonar et al. |
| 2017/0105646 A1 | 4/2017 | Bryenton et al. |
| 2017/0124279 A1 | 5/2017 | Rothman |
| 2017/0156658 A1 | 6/2017 | Maharbiz et al. |
| 2017/0172489 A1 | 6/2017 | Afentakis |
| 2017/0188841 A1 | 7/2017 | Ma et al. |
| 2017/0238849 A1 | 8/2017 | Chapman et al. |
| 2017/0245799 A1 | 8/2017 | Fleischer et al. |
| 2017/0255812 A1 | 9/2017 | Kwon |
| 2017/0311807 A1 | 11/2017 | Fu et al. |
| 2017/0319066 A1 | 11/2017 | Ver Steeg |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0220924 A1 | 8/2018 | Burns et al. |
| 2018/0220953 A1 | 8/2018 | Burns et al. |
| 2018/0220954 A1 | 8/2018 | Burns et al. |
| 2018/0220961 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0053751 A1 | 2/2019 | Torres |
| 2019/0060602 A1 | 2/2019 | Tran et al. |
| 2019/0069836 A1 | 3/2019 | Hettrick |
| 2019/0104981 A1 | 4/2019 | Sarrafzadeh et al. |
| 2019/0104982 A1 | 4/2019 | Dunn et al. |
| 2019/0117964 A1 | 4/2019 | Bahrami et al. |
| 2019/0134396 A1 | 5/2019 | Toth et al. |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0008299 A1 | 1/2020 | Tran et al. |
| 2020/0043607 A1 | 2/2020 | Zerhusen et al. |
| 2020/0069240 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |

(56) References Cited

U.S. PATENT DOCUMENTS

| | | |
|---|---|---|
| 2020/0127398 A1 | 4/2020 | Burns et al. |
| 2020/0296821 A1 | 9/2020 | Trublowski et al. |
| 2020/0297244 A1 | 9/2020 | Brownhill et al. |
| 2020/0297255 A1 | 9/2020 | Martinez et al. |
| 2021/0076974 A1 | 3/2021 | Burns |
| 2021/0159621 A1 | 5/2021 | Burns et al. |
| 2021/0204864 A1 | 7/2021 | Burns et al. |
| 2021/0307635 A1 | 10/2021 | Burns |
| 2022/0071555 A1 | 3/2022 | Burns et al. |
| 2022/0192587 A1 | 6/2022 | Burns et al. |
| 2022/0211291 A1 | 7/2022 | Tonar et al. |
| 2022/0240840 A1 | 8/2022 | Burns |
| 2022/0273238 A1 | 9/2022 | Burns et al. |
| 2022/0285865 A1 | 9/2022 | Burns et al. |
| 2022/0287584 A1 | 9/2022 | Burns et al. |
| 2022/0330847 A1 | 10/2022 | Burns et al. |
| 2022/0409086 A1 | 12/2022 | Burns |
| 2023/0068683 A1 | 3/2023 | Burns et al. |
| 2023/0109698 A1 | 4/2023 | Tonar et al. |
| 2023/0148893 A1 | 5/2023 | Burns et al. |
| 2023/0363698 A9 | 5/2023 | Burns |
| 2023/0337966 A1 | 6/2023 | Sarrafzadeh et al. |
| 2023/0240592 A1 | 8/2023 | Burns et al. |
| 2023/0329629 A1 | 10/2023 | Burns et al. |
| 2023/0335929 A1 | 10/2023 | Burns et al. |
| 2023/0346240 A1 | 11/2023 | Tonar et al. |
| 2024/0039192 A1 | 2/2024 | Burns et al. |
| 2024/0081727 A1 | 3/2024 | Burns |
| 2024/0138696 A1 | 5/2024 | Burns et al. |
| 2024/0225529 A1 | 7/2024 | Burns |
| 2024/0268753 A1 | 8/2024 | Burns et al. |
| 2024/0389932 A1 | 11/2024 | Burns et al. |

FOREIGN PATENT DOCUMENTS

| | | |
|---|---|---|
| CA | 2609842 C | 10/2016 |
| CN | 102033166 A | 4/2011 |
| CN | 204119175 U | 1/2015 |
| CN | 104352230 A | 2/2015 |
| CN | 104567657 A | 4/2015 |
| CN | 104644125 A | 5/2015 |
| CN | 105578333 A | 5/2016 |
| CN | 105963074 A | 9/2016 |
| CN | 208111467 U | 11/2018 |
| DE | 102012011212 A1 | 1/2012 |
| EP | 0970656 A1 | 1/2000 |
| EP | 1080687 A1 | 3/2001 |
| EP | 1372475 B1 | 1/2004 |
| EP | 1569553 A1 | 9/2005 |
| EP | 3092946 A1 | 11/2016 |
| EP | 3280488 B1 | 12/2018 |
| GB | 2148513 | 5/1985 |
| GB | 2584808 A | 12/2020 |
| JP | H06-502323 | 3/1994 |
| JP | H10-201726 | 8/1998 |
| JP | 2000-060805 A | 2/2000 |
| JP | 2001-178705 | 7/2001 |
| JP | 2001-326773 A | 11/2001 |
| JP | 2003-169787 A | 6/2003 |
| JP | 2003-169788 A | 6/2003 |
| JP | 2003-202312 | 7/2003 |
| JP | 2003-290166 A | 10/2003 |
| JP | 2005-52227 | 3/2005 |
| JP | 2009-268611 A | 11/2009 |
| JP | 4418419 | 2/2010 |
| JP | 2013-528428 | 7/2013 |
| JP | 2013-198639 A | 10/2013 |
| JP | 2015-509028 | 3/2015 |
| JP | 2015-134074 | 7/2015 |
| JP | 2016-519969 | 7/2016 |
| JP | 2016-527943 A | 9/2016 |
| KR | 10-2014-0058445 | 5/2014 |
| WO | 96/10951 A1 | 4/1996 |
| WO | 2001/054580 A1 | 8/2001 |
| WO | 2002/080770 A1 | 10/2002 |
| WO | 2004/105602 A1 | 12/2004 |
| WO | 2005/099644 A2 | 10/2005 |
| WO | 2006/029035 A1 | 3/2006 |
| WO | 2007/098762 A1 | 9/2007 |
| WO | 2009/144615 A1 | 12/2009 |
| WO | 2010/060102 A2 | 5/2010 |
| WO | 2011/004165 A1 | 1/2011 |
| WO | 2011/022418 A2 | 2/2011 |
| WO | 2011/048556 A2 | 4/2011 |
| WO | 2011/080080 A1 | 7/2011 |
| WO | 2011/080262 A1 | 7/2011 |
| WO | 2011/084722 A1 | 7/2011 |
| WO | 2011/091517 A1 | 8/2011 |
| WO | 2011/143071 A2 | 11/2011 |
| WO | 2013/033724 A1 | 3/2013 |
| WO | 2013/114356 A1 | 8/2013 |
| WO | 2013/116242 A2 | 8/2013 |
| WO | 2013/140714 A1 | 9/2013 |
| WO | 2014/186894 A1 | 11/2014 |
| WO | 2015/003015 A2 | 1/2015 |
| WO | 2015/022583 A2 | 2/2015 |
| WO | 2015/077838 A1 | 6/2015 |
| WO | 2015/168720 A1 | 11/2015 |
| WO | 2015/169911 A1 | 11/2015 |
| WO | 2015/195720 A1 | 12/2015 |
| WO | 2016/098062 A1 | 6/2016 |
| WO | 2016/172263 A1 | 10/2016 |
| WO | 2016/172264 A1 | 10/2016 |
| WO | 2017/032393 | 3/2017 |
| WO | 2017/214188 A1 | 12/2017 |
| WO | 2017/218818 A2 | 12/2017 |
| WO | 2018/071715 A1 | 4/2018 |
| WO | 2018/077560 A1 | 5/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | 2018/168424 A1 | 9/2018 |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 | 5/2019 |
| WO | 2019/099812 A1 | 5/2019 |
| WO | 2019/113481 | 6/2019 |
| WO | 2019/157290 | 8/2019 |
| WO | 2019/162272 A1 | 8/2019 |
| WO | 2020/014779 A1 | 1/2020 |
| WO | 2020/043806 A1 | 3/2020 |
| WO | 2020/053290 A1 | 3/2020 |
| WO | 2020/077100 A1 | 4/2020 |
| WO | 2020/187643 A1 | 9/2020 |
| WO | 2020/187851 A1 | 9/2020 |
| WO | 2020/234429 A2 | 11/2020 |

OTHER PUBLICATIONS

Brem et al., "Protocol for the successful treatment of pressure ulcers", Jul. 2004, pp. 9S-17S (Year: 2004).*

Liu, "A systematic review of electrical stimulation for pressure ulcer prevention and treatment in people with spinal cord injuries", 2014, pp. 703-718 (Year: 2014).*

Rotaru, "Friction between human skin and medical textiles for decubitus prevention", 2013, pp. 91-96 (Year: 2013).*

Thomas, "Prevention and Treatment of Pressure Ulcers", 2006, pp. 46-59 (Year: 2006).*

Truong, "Pressure Ulcer Prevention in the Hospital Setting Using Silicone Foam Dressings", 2016, pp. 1-6 (Year: 2016).*

(56) References Cited

OTHER PUBLICATIONS

Tur, "Topical hydrogen peroxide treatment of ischemic ulcers in the guinea pig: Blood recruitment in multiple skin sites", 1995, pp. 217-221 (Year: 1995).*

Alanen, "Measurement of Hydration in the Stratum Corneum with the MoistureMeter and Comparison with the Corneometer," *Skin Research and Technology,* 10:32-37 (2004), Submitted in parent application U.S. Appl. No. 16/193,707.

Alberts et al., "The Extracellular Matrix of Animals," *Molecular Biology of the Cell,* 4th ed., pp. 1065-1127 (2002), Submitted in parent application U.S. Appl. No. 16/193,707.

Allman et al., "Pressure Ulcer Risk Factors Among Hospitalized Patients with Activity Limitation," *JAMA,* 273:865-870 (1995), Submitted in parent application U.S. Appl. No. 16/193,707.

Anonymous, "Recommended Practices for Positioning the Patient in the Perioperative Practice Setting," in *Perioperative Standards, Recommended Practices, and Guidelines,* AORN, Inc., 525-548 (2006), Submitted in parent application U.S. Appl. No. 16/193,707.

Arao et al., "Morphological Characteristics of the Dermal Papillae In the Development of Pressure Sores," *World Wide Wounds,* (1999), Submitted in parent application U.S. Appl. No. 16/193,707.

Australian Intellectual Property Office, Office Action issued on May 1, 2014 for corresponding Australian patent application No. 2011253253 (pp. 1-10) and pending claims (pp. 11-15) pp. 1-15, Submitted in parent application U.S. Appl. No. 16/193,707.

Australian Patent Office, Office Action issued on Jun. 1, 2015, for corresponding Australian Patent Application No. 2011253253 (pp. 1-4) and claims (pp. 5-10) pp. 1-10, Submitted in parent application U.S. Appl. No. 16/193,707.

Bader et al., "Effect of Externally Applied Skin Surface Forces on Tissue Vasculature," *Archives of Physical Medicine and Rehabilitation,* 67(11):807-11 (1986), Submitted in parent application U.S. Appl. No. 16/193,707.

Barnes, "Moisture Meters for Use on Thin Lumber and Veneers," *Moisture Register Co.,* 1-5 (1956), Submitted in parent application U.S. Appl. No. 16/193,707.

Bates-Jensen et al., "Subepidermal Moisture Predicts Erythema and Stage 1 Pressure Ulcers in Nursing Home Residents: A Pilot Study," *Journal of the American Geriatric Society,* 55:1199-1205 (2007), Submitted in parent application U.S. Appl. No. 16/193,707.

Bates-Jensen et al., "Subepidermal moisture differentiates erythema and stage 1 pressure ulcers in nursing home residents," *Wound Repair Regeneration,* 16:189-197 (2008), Submitted in parent application U.S. Appl. No. 16/193,707.

Bates-Jensen et al., "Subepidermal Moisture Is Associated With Early Pressure Ulcer Damage in Nursing Home Residents With Dark Skin Tones; Pilot Findings," *Journal of Wound Ostomy and Continence Nursing,* 36(3):277-284 (2009), Submitted in parent application U.S. Appl. No. 16/193,707.

Bergstrand et al., "Pressure-induced Vasodilation and Reactive Hyperemia at Different Depths in Sacral Tissue Under Clinically Relevant Conditions," *Microcirculation,* 21:761-771 (2014), Submitted in parent application U.S. Appl. No. 16/193,707.

Bergstrom et al., "Pressure Ulcers in Adults: Prediction and Prevention," *Clinical Practice Guideline—Quick Reference Guide for Clinicians,* 117 (1992), Submitted in parent application U.S. Appl. No. 16/193,707.

Brem et al., "High cost of stage IV pressure ulcers," *American Journal of Surgery,* 200:473-477 (2010), Submitted in parent application U.S. Appl. No. 16/193,707.

Brienza et al., "Friction-Induced Skin Injuries—Are They Pressure Ulcers?," *Journal of Wound Ostomy and Continence Nursing,* 42(1):62-64 (2015), Submitted in parent application U.S. Appl. No. 16/193,707.

Carmo-Araujo et al., "Ischaemia and reperfusion effects on skeletal muscle tissue: morphological and histochemical studies," *International Journal of Experimental Pathology,* 88:147-154 (2007), Submitted in parent application U.S. Appl. No. 16/193,707.

Ceelen et al., "Compression-induced damage and internal tissue strains are related," *Journal of Biomechanics,* 41:3399-3404 (2008), Submitted in parent application U.S. Appl. No. 16/193,707.

Ching et al., "Tissue electrical properties monitoring for the prevention of pressure sore" *Prosthetics and Orthotics International,* 35(4):386-394 (2011), Submitted in parent application U.S. Appl. No. 16/193,707.

Clendenin et al., "Inter-operator and inter-device agreement and reliability of the SEM Scanner," *Journal of Tissue Viability,* 24(1):17-23 (2015), Submitted in parent application U.S. Appl. No. 16/193,707.

De Lorenzo et al., "Predicting body cell mass with bioimpedance by using theoretical methods: a technological review," *Journal of Applied Physiology,* 82(5):1542-1558 (1997), Submitted in parent application U.S. Appl. No. 16/193,707.

Demarre et al., "The cost of pressure ulcer prevention and treatment in hospitals and nursing homes in Flanders: A cost-of-illness study," *International Journal of Nursing Studies,* 1-14 (2015), Submitted in parent application U.S. Appl. No. 16/193,707.

Dodde et al., "Bioimpedance of soft tissue under compression," *Physiology Measurement,* 33(6):1095-1109 (2012), Submitted in parent application U.S. Appl. No. 16/193,707.

DuPont, "General Specifications for Kapton Polyimide Film," Retrieved from Dupont: http://www2.dupont.com/Kapton/en_US/assets/ downloads/pdf/Gen_Specs.pdf, pp. 1-7 (2012), Submitted in parent application U.S. Appl. No. 16/193,707.

Dupont, "Pyralux® FR Coverlay, Bondply & Sheet Adhesive," webpage, Retrieved from: www2.dupont.com/Pyralux/en_US/ products/adhesives_films/FR/FR_films_html pp. 1-2 (2012), Submitted in parent application U.S. Appl. No. 16/193,707.

DuPont, "Pyralux® FR Copper-clad Laminate," webpage, Retrieved from: www2.dupont.com/Pyraluxlen_US/ productsllaminate/FR/ pyralux_fr.html, pp. 1-2 (2012), Submitted in parent application U.S. Appl. No. 16/193,707.

Eberlein-Gonska et al., "The Incidence and Determinants of Decubitus Ulcers in Hospital Care: An Analysis of Routine Quality Management Data at a University Hospital," *Deutsches Arzteblatt International,* 110(33-34):550-556, (2013), Submitted in parent application U.S. Appl. No. 16/193,707.

European Patent Office, ESSR issued on Aug. 22, 2014 for corresponding European Patent Application No. 117811061.4 (pp. 1-7) and pending claims (pp. 3-10) pp. 1-10, Submitted in parent application U.S. Appl. No. 16/193,707.

European Patent Office, Office Action issued on Jul. 13, 2015, for corresponding European Patent Application No. 117811061.4 (pp. 1-5) and claims (pp. 6-9) pp. 1-9, Submitted in parent application U.S. Appl. No. 16/193,707.

Extended European Search Report dated Aug. 19, 2016, in European Patent Application No. 16169670, Submitted in parent application U.S. Appl. No. 16/193,707.

Extended European Search Report dated Sep. 19, 2016, in European Patent Application No. 16166483.4, Submitted in parent application U.S. Appl. No. 16/193,707.

Extended European Search Report dated Mar. 13, 2017, in European Patent Application No. 16196899.5, Submitted in parent application U.S. Appl. No. 16/193,707.

Gabriel, "Compilation of the Dielectric Properties of Body Tissues at Rf and Microwave Frequencies Report," *Occupational and Environmental Health Directorate,* (1996), Submitted in parent application U.S. Appl. No. 16/193,707.

Gabriel et al., "The dielectric properties of biological tissues: II. Measurements in the frequency range 10 Hz to 20 GHz," *Physics in Medicine and Biology,* 41:2251-69 (1996), Submitted in parent application U.S. Appl. No. 16/193,707.

Gardiner et al., "Incidence of hospital-acquired pressure ulcers—a population-based cohort study," *International Wound Journal,* 11(6):696-700 (2014), Submitted in parent application U.S. Appl. No. 16/193,707.

Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014), Submitted in parent application U.S. Appl. No. 16/193,707.

(56) References Cited

OTHER PUBLICATIONS

Gonzalez-Correa et al., "Electrical bioimpedance readings increase with higher pressure applied to the measuring probe," *Physiology Measurement*, 26:S39-S47 (2005), Submitted in parent application U.S. Appl. No. 16/193,707.

Guihan et al., "Assessing the feasibility of subepidermal moisture to predict erythema and stage 1 pressure ulcers in persons with spinal cord injury: A pilot study," *Journal of Spinal Cord Medicine*, 35(1):46-52 (2012), Submitted in parent application U.S. Appl. No. 16/193,707.

Harrow, "Subepidermal moisture surrounding pressure ulcers in persons with a spinal cord injury: A pilot study," *Journal of Spinal Cord Medicine*, 37(6):719-728 (2014), Submitted in parent application U.S. Appl. No. 16/193,707.

Houwing et al., "Pressure-induced skin lesions in pigs: reperfusion injury and the effects of vitamin E," *Journal of Wound Care*, 9(1):36-40 (2000), Submitted in parent application U.S. Appl. No. 16/193,707.

Huang et al., "A device for skin moisture and environment humidity detection," *Sensors and Actuators B: Chemical*, 206-212 (2008), Submitted in parent application U.S. Appl. No. 16/193,707.

International Search Report dated Apr. 12, 2018, issued in International Patent Application No. PCT/US2018/016731, Submitted in parent application U.S. Appl. No. 16/193,707.

International Search Report dated Apr. 12, 2018, issued in International Patent Application No. PCT/US2018/016738, Submitted in parent application U.S. Appl. No. 16/193,707.

International Search Report dated Apr. 26, 2018, issued in International Patent Application No. PCT/US2018/016741, Submitted in parent application U.S. Appl. No. 16/193,707.

International Search Report dated Jul. 12, 2018, issued in International Patent Application No. PCT/US2018/016736, Submitted in parent application U.S. Appl. No. 16/193,707.

International Search Report dated Sep. 10, 2018, issued in International Patent Application No. PCT/US2018/038055, Submitted in parent application U.S. Appl. No. 16/193,707.

International Search Report dated Jan. 29, 2019 issued in International Patent Application No. PCT/US2018/061494, Submitted in parent application U.S. Appl. No. 16/193,707.

International Search Report dated Feb. 5, 2019, issued in International Patent Application No. PCT/US2018/064527, Submitted in parent application U.S. Appl. No. 16/193,707.

International Search Report dated Feb. 11, 2019, issued in International Patent Application No. PCT/US2018/061497, Submitted in parent application U.S. Appl. No. 16/193,707.

International Search Report dated May 29, 2019, issued in International Patent Application No. PCT/US2019/017226, Submitted in parent application U.S. Appl. No. 16/193,707.

International Search Report and Written Opinion issued on Feb. 9, 2012 for International Patent Application No. PCT/US2011/035618, Submitted in parent application U.S. Appl. No. 16/193,707.

International Search Report and Written Opinion issued on Jul. 22, 2016, for International Patent Application No. PCT/US2016/28515, Submitted in parent application U.S. Appl. No. 16/193,707.

International Search Report and Written Opinion issued on Jul. 26, 2016, for International Patent Application No. PCT/US2016/28515, Submitted in parent application U.S. Appl. No. 16/193,707.

Jan et al., "Local cooling reduces skin ischemia under surface pressure in rats: an assessment by wavelet analysis of laser Doppler blood flow oscillations," *Physiology Measurement*, 33(10):1733-1745 (2012), Submitted in parent application U.S. Appl. No. 16/193,707.

Jaskowski, "Evaluation of the Healing Process of Skin Wounds by Means of Skin Absolute Value of Electrical Impedance," *Dermatol. Mon.schr.*, 172(4):223-228 (1986), Submitted in parent application U.S. Appl. No. 16/193,707.

Jiang et al., "Expression of cytokines, growth factors and apoptosis-related signal molecules in chronic pressure ulcer wounds healing," *Spinal Cord*, 52(2):145-151 (2014), Submitted in parent application U.S. Appl. No. 16/193,707.

Jiang et al., "Ischemia-Reperfusion Injury-Induced Histological Changes Affecting Early Stage Pressure Ulcer Development in a Rat model," *Ostomy Wound Management*, 57:55-60 (2011), Submitted in parent application U.S. Appl. No. 16/193,707.

Jiricka et al., "Pressure Ulcer Risk factors in an ICU Population," *American Journal of Critical Care*, 4:361-367 (1995), Submitted in parent application U.S. Appl. No. 16/193,707.

Kanai et al., "Electrical measurement of fluid distribution in legs and arms," *Medical Progress through Technology Journal*, 12:159-170 (1987), Submitted in parent application U.S. Appl. No. 16/193,707.

Kasuya et al., "Potential application of in vivo imaging of impaired lymphatic duct to evaluate the severity of pressure ulcer in mouse model," *Scientific Reports*, 4:4173 (7 pages) (2014), Submitted in parent application U.S. Appl. No. 16/193,707.

Lee, "CapSense Best Practices," *Application Note 2394*, 1-10 (2007), Submitted in parent application U.S. Appl. No. 16/193,707.

Loerakker et al., "The effects of deformation, ischemia, and reperfusion on the development of muscle damage during prolonged loading," *Journal of Applied Physiology*, 111(4):1168-1177 (2011), Submitted in parent application U.S. Appl. No. 16/193,707.

Loerakker et al., "Temporal Effects of Mechanical Loading on Deformation-Induced Damage in Skeletal Muscle Tissue," *Annual Review of Biomedical Engineering*, 38(8):2577-2587 (2010), Submitted in parent application U.S. Appl. No. 16/193,707.

Lyder et al., "Quality of Care for Hospitalized Medicare Patients at Risk for Pressure Ulcers," *Archives of Internal Medicine*, 161:1549-1554 (2001), Submitted in parent application U.S. Appl. No. 16/193,707.

Martinsen, "Bioimpedance and Bioelectricity Basics," *Elsevier Academic Press*, Chapters 1 and 10 (2015), Submitted in parent application U.S. Appl. No. 16/193,707.

Mathiesen et al., "Are labour-intensive efforts to prevent pressure ulcers cost-effective?" *Journal of Medical Economics*, 16(10):1238-1245 (2013), Submitted in parent application U.S. Appl. No. 16/193,707.

Matthie et al., "Analytic assessment of the various bioimpedance methods used to estimate body water," *Journal of Applied Physiology*, 84(5):1801-1816 (1998), Submitted in parent application U.S. Appl. No. 16/193,707.

Miller et al., "Lymphatic Clearance during Compressive Loading," *Lymphology*, 14(4):161-166 (1981), Submitted in parent application U.S. Appl. No. 16/193,707.

Moore et al., "A randomised controlled clinical trial of repositioning, using the 30° tilt, for the prevention of pressure ulcers," *Journal of Clinical Nursing*, 20:2633-2644 (2011), Submitted in parent application U.S. Appl. No. 16/193,707.

Moore et al., "Pressure ulcer prevalence and prevention practices in care of the older person in the Republic of Ireland," *Journal of Clinical Nursing*, 21:362-371 (2012), Submitted in parent application U.S. Appl. No. 16/193,707.

Moore et al., "A review of PU prevalence and incidence across Scandinavia, Iceland and Ireland (Part I)", *Journal of Wound Care*, 22(7):361-362, 364-368 (2013), Submitted in parent application U.S. Appl. No. 16/193,707.

Mulasi, "Bioimpedance at the Bedside: Current Applications, Limitations, and Opportunities," *Nutritional Clinical Practice*, 30(2):180-193 (2015), Submitted in parent application U.S. Appl. No. 16/193,707.

National Pressure Ulcer Advisory Panel et al., "Prevention and Treatment of Pressure Ulcers: Clinical Practice Guideline," *Cambridge Media*, (2014), Submitted in parent application U.S. Appl. No. 16/193,707.

Nixon et al., "Pathology, diagnosis, and classification of pressure ulcers: comparing clinical and imaging techniques," *Wound Repair and Regeneration*, 13(4):365-372 (2005), Submitted in parent application U.S. Appl. No. 16/193,707.

Nuutinen et al., "Validation of a new dielectric device to asses changes of tissue water in skin and subcutaneous fat," *Physiological Measurement*, 25:447-454 (2004), Submitted in parent application U.S. Appl. No. 16/193,707.

O'Goshi, "Skin conductance; validation of Skicon-200EX compared to the original model, Skicon-100," *Skin Research and Technology*, 13:13-18 (2007), Submitted in parent application U.S. Appl. No. 16/193,707.

(56) References Cited

OTHER PUBLICATIONS

Oomens et al., "Pressure Induced Deep Tissue Injury Explained," *Annual Review of Biomedical Engineering*, 42(2):297-305 (2015), Submitted in parent application U.S. Appl. No. 16/193,707.
Scallan et al., "Chapter 4: Pathophysiology of Edema Formation," *Capillary Fluid Exchange: Regulation, Functions, and Pathology*, 47-61 (2010), Submitted in parent application U.S. Appl. No. 16/193,707.
Schultz et al., "Extracellular matrix: review of its role in acute and chronic wounds," *World Wide Wounds*, 1-20 (2005), Submitted in parent application U.S. Appl. No. 16/193,707.
Schwan, "Electrical properties of tissues and cells," *Advances in Biology and Medical Physics*, 15:148-199 (1957), Submitted in parent application U.S. Appl. No. 16/193,707.
Sener et al., "Pressure ulcer-induced oxidative organ injury is ameliorated by beta-glucan treatment in rats," *International Immunopharmacology*, 6(5):724-732 (2006), Submitted in parent application U.S. Appl. No. 16/193,707.
Sewchuck et al., "Prevention and Early Detection of Pressure Ulcers in Patients Undergoing Cardiac Surgery," *AORN Journal*, 84(1):75-96 (2006), Submitted in parent application U.S. Appl. No. 16/193,707.
Sprigle et al., "Analysis of Localized Erythema Using Clinical Indicators and Spectroscopy," *Ostomy Wound Management*, 49:42-52 (2003), Submitted in parent application U.S. Appl. No. 16/193,707.
Stekelenburg et al., "Deep Tissue Injury: How Deep is Our Understanding?" *Archives of Physical Medicine Rehabilitation*, 89(7):1410-1413 (2008), Submitted in parent application U.S. Appl. No. 16/193,707.
Stekelenburg et al., "Role of ischemia and deformation in onset of compression-induced deep tissue injury MRI-based studies in a rat model," *Journal of Applied Physiology*, 102:2002-2011 (2007), Submitted in parent application U.S. Appl. No. 16/193,707.
Swisher et al., "Impedance sensing device enables early detection of pressure ulcers in vivo," *Nature Communications*, 6:6575-6584 (2015), Submitted in parent application U.S. Appl. No. 16/193,707.
Thomas et al., "Hospital-Acquired Pressure Ulcers and Risk of Death," *Journal of the American Geriatrics Society*, 44:1435-1440 (1996), Submitted in parent application U.S. Appl. No. 16/193,707.
Valentinuzzi et al., "Bioelectrical Impedance Techniques in Medicine. Part II: Monitoring of Physiological Events by Impedance," *Critical Reviews in Biomedical Engineering*, 24(4-6):353-466 (1996), Submitted in parent application U.S. Appl. No. 16/193,707.
Vangilder et al., "Results of Nine International Pressure Ulcer Prevalence Surveys: 1989 to 2005," *Ostomy Wound Management*, 54(2):40-54 (2008), Submitted in parent application U.S. Appl. No. 16/193,707.
Wagner et al., "Bioelectrical Impedance as a Discriminator of Pressure Ulcer Risk," *Advances in Wound Care*, 9(2):30-37 (1996), Submitted in parent application U.S. Appl. No. 16/193,707.
Wang, "Biomedical System for Monitoring Pressure Ulcer Development," UCLA Electronic Theses and Dissertations, California, USA, pp. 1-123 (2013), Submitted in parent application U.S. Appl. No. 16/193,707.
Watanabe et al., "CT analysis of the use of the electrical impedance technique to estimate local oedema in the extremities in patients with lymphatic obstruction," *Medical and Biological Engineering and Computing*, 36(1):60-65 (1998), Submitted in parent application U.S. Appl. No. 16/193,707.
Weiss, "Tissue destruction by neutrophils," *The New England Journal of Medicine*, 320(6):365-76 (1989), Submitted in parent application U.S. Appl. No. 16/193,707.
Extended European Search Report dated Oct. 25, 2019, in European Patent Application No. 19186393.5, Herewith.
Extended European Search Report dated Feb. 6, 2020, in European Patent Application No. 18748733.5, Herewith.
Extended European Search Report dated Feb. 10, 2020, in European Patent Application No. 18748512.3, Herewith.
Ford, "Hospice Wins Award for Innovation in Pressure Ulcer Prevention," *Nursing Times*, downloaded and printed on Apr. 18, 2020, from https://www.nursingtimes.net/news/research-and-innovation/hospice-wins-award-for-innovation-in-pressure-ulcer-prevention-30-11-2018/ (2018), Herewith.
International Search Report dated Mar. 9, 2020, issued in International Patent Application No. PCT/US2019/055655, Herewith.
Moore et al., "SEM Scanner Made Easy," *Wounds International*, pp. 1-6, available at www.woundsinternational.com (2018), Herewith.
Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151, 49 pp. (Aug. 2019), Herewith.
Supplementary Partial European Search Report dated Jan. 27, 2020, in European Patent Application No. 18747707, Herewith.
Extended European Search Report dated Nov. 19, 2019, in European Patent Application No. 19190000.0, Herewith.
Extended European Search Report dated Feb. 10, 2019, in European Patent Application No. 18748025.6, Herewith.
Extended European Search Report dated Jun. 24, 2020, in European Patent Application No. 18747707.0, Herewith.
Great Britain Search Report dated Apr. 27, 2020, in Great Britain Patent Applicaton No. GB2002889.0, Herewith.
Vowden et al., "Diabetic Foot Ulcer or Pressure Ulcer? That Is the Question," *The Diabetic Foot Journal*, 18:62-66 (2015), Herewith.
Wang et al., "A Wireless Biomedical Instrument for Evidence-Based Tissue Wound Characterization," *Wireless Health*, pp. 222-223 (2010), Herewith.
Zanibbi, "Pattern Recognition: An Overview," downloaded from https://www.cs.rit.edu/~rlaz/prec20092/slides/Overview.pdf, 30 pp. (2010), Herewith.
Bates-Jensen et al., "Subepidermal Moisture Detection of Pressure Induced Tissue Damage on the Trunk: The Pressure Ulcer Detection Study Outcomes," *Wound Repair and Regeneration*, 25:502-511 (2017), Herewith.
Black et al., "Differential Diagnosis of Suspected Deep Tissue Injury," *International Wound Journal*, 13(4):531-539 (2015), Herewith.
Great Britain Search Report dated Jun. 28, 2021, in Great Britain Patent Application No. GB2106848.1, Herewith.
Hou, "Section IV. Osteofascial Compartment Syndrom," *Limbs Trauma*, 7:215-217 (2016), Herewith.
International Search Report dated Dec. 8, 2020, issued in International Patent Application PCT/US2020/051134, Herewith.
International Search Report dated Aug. 17, 2021, issued in International Patent Application PCT/US2021/023818, Herewith.
Moore et al., "Subepidermal Moisture (SEM) and Bioimpedance: A Literature Review of a Novel Method for Early Detection of Pressure-Induced Tissue Damage (Pressure Ulcers)," *International Wound Journal*, 14(2):331-337 (2016), Herewith.
Oliveira, "The Accuracy of Ultrasound, Thermography, Photography and Sub-Epidermal Moisture as a Predictor of Pressure Ulcer Presence—a Systematic Review," RCSI, School of Nursing thesis (2015), Herewith.
Saxena, *The Pocket Doctor: Obstetrics & Gynecology*, pp. 76-77 (2017), Herewith.
Supplementary European Search Report dated Jul. 13, 2021, in European Patent Application No. 18887039, Herewith.
Supplementary European Search Report dated Oct. 1, 2021, in European Patent Application No. 19751130, Herewith.
Yang, *Handbook of Practical Burn Surgery*, p. 48 (2008), Herewith.
De Oliveira et al., "Sub-epidermal moisture versus tradition and visual skin assessments to assess pressure ulcer risk in surgery patients" *Journal of Wound Care*, 31(3):254-264 (2022), Herewith.
Extended European Search Report dated Mar. 17, 2022, in European Patent Application No. 19838240.0, Herewith.
Extended European Search Report dated May 24, 2022, in European Patent Application No. 19871332.3, Herewith.
Great Britain Search Report dated Feb. 9, 2022, in Great Britain Patent Application No. GB2118088.0, Herewith.
Great Britain Search Report dated Feb. 14, 2022, in Great Britain Patent Application No. GB2118092.2, Herewith.

(56) References Cited

OTHER PUBLICATIONS

International Search Report mailed May 13, 2022, issued in International Patent Application PCT/US2022/014913, Herewith.
Moore, "Using SEM (Sub Epidermal Moisture) Measurement for Early Pressure Ulcer Detection" Institute for Pressure Injury Prevention, WCICT 2017 (Jun. 20-21), Manchester, UK, 7 pp., available at www.pressureinjuryprevention.com/wp-content/uploads/2017/07/ipip_Moore_Sub_Epidermal_Moisture_notes.pdf (2017), Herewith.
Musa et al., "Clinical Impact of a Sub-Epidermal Moisture Scanner: What is the Real-World Use?," *J. Wound Care,* 30(3):2-11 (2012) (JWC Proof), Herewith.
Truong et al., "Pressure Ulcer Prevention in the Hospital Setting Using Silicone Foam Dressings," *Cureus,* 8(8):e730, pp. 1-6 (2016), Herewith.
Tur et al., "Topical Hydrogen Peroxide Treatment of Ischemic Ulcers in the Guinea Pig: Blood Recruitment in Multiple Skin Sites," *J. Am. Acad. Dermatol.,* 33:217-221 (1995), Herewith.
Vangilder et al., "Results of Nine International PRessure Ulcer Prevalence Surveys: 1989 to 2005," *Ostomy Wound Management,* 54(2):40-54 (2008), Herewith.
De Oliveira et al., "Sub-epidermal moisture versus tradition and visual skin assessments to assess pressure ulcer risk in surgery patients," Journal of Wound Care, 31(3):254-264 (2022), Mark Allen Group (pub.) (obtained online), Submitted in parent application U.S. Appl. No. 16/193,707.
Hamazoto et al., "Estimate of Burn Depth by Non-Invasive Capacitance Measurement," *Japan Soc. ME & BE,* 42:266 (Jun. 2003), Herewith.
International Search Report mailed Aug. 2, 2022, issued in International Patent Application PCT/US2022/025508, Herewith.
International Search Report mailed Aug. 15, 2022, issued in International Patent Application PCT/US2022/019338, Herewith.
Pang et al., (eds.) Diagnosis and Treatment of Diabetes, China Press of Traditional Chinese Medicine (publisher), Beijing, China, pp. 466-468 (Oct. 2016), with English Translation, Herewith.
Extended European Search Report dated Feb. 1, 2023, in European Patent Application No. 22211200, Herewith.
Arimoto et al., "Non-Contact Skin Moisture Measurement Based on Near-Infrared Spectroscopy," *Applied Spectroscopy,* 58(12):1439-1446 (2004), Herewith.
Extended European Search Report completed Nov. 7, 2023, in European Patent Application No. 23188775.3, Herewith.
Partial European Search Report dated Sep. 6, 2023, in European Patent Application No. 23188775.3, Herewith.
Ross et al., "Assessment of Sub-Epidermal Moisture by Direct Measurement of Tissue Biocapacitance," *Medical Engineering & Physics,* 73:92-99 (Jul. 26, 2019), Herewith.
Supplementary Partial European Search Report dated Jan. 10, 2024, in European Patent Application No. 21782145, Herewith.
Avci et al., "Low-Level Laser (Light) Therapy (LLLT) in Skin: Stimulating, Healing, Restoring," *Seminars in Cutaneous Medicine and Surgery,* 32(1)41-52 (Mar. 2013), Herewith.
Brunetti et al., "Validation of a sub-epidermal moisture scanner for early detection of pressure ulcers in an ex vivo porcine model of localized oedema," *J. Tissure Viability,* 32(4)508-515 (available online Jul. 8, 2023), Herewith.
Byrne et al., "Sub epidermal moisture measurement and targeted SSKIN bundle interventions, a winning combination for the treatment of early pressure ulcer development," *Int. Wound J.,* 2022:1-13 (published online Nov. 25, 2022), Herewith.
Chan et al., "Using Wireless Measuring Devices and Tablet PC to Improve the Efficiency of Vital Signs Data Collection in Hospital," 4 pp., 2014 IEEE International Symposium on Bioelectronics and Bioinformatics (IEEE ISBB 2014), Herewith.
Extended European Search Report dated Jun. 11, 2024, in European Patent Application No. 24158801.1, Herewith.
International Search Report mailed May 29, 2024, in International Patent Application PCT/US2023/074190, Herewith.
Lustig et al., "A maching learning algorithm for early detection of heel deep tissue injuries based on a daily history of sub-epidermal moisture measurements," *Int. Wound J.,* 2021:1-10 (published online Dec. 1, 2021), Herewith.
Partial European Search Report completed Mar. 27, 2024, in European Patent Application No. 23208591.0, Herewith.
Partial European Search Report completed Apr. 16, 2024, in European Patent Application No. 24151800.0, Herewith.
Supplementary European Search Report completed May 8, 2024, in European Patent Application No. 21782145, Herewith.
Visscher et al., "Face Masks for Noninvasive Ventilation: Fit, Excess Skin Hydration, and Pressure Ulcers," *Respiratory Care,* 60(11):1536-1547 (Nov. 2015), Herewith.
Weber et al., "Remote Wound Monitoring of Chronic Ulcers," IEEE Transactions on Information Technology in Biomedicine, IEEE Service Center, Los Alamitos, CA, vol. 13(2):371-377 (Mar. 1, 2010), Herewith.
U.S. Appl. No. 16/193,707, filed Nov. 16, 2018, which is abandoned.
U.S. Appl. No. 18/159,068, filed Jan. 24, 2023, which is pending.
U.S. Appl. No. 18/506,817, filed Nov. 10, 2023, which is pending.
U.S. Appl. No. 17/531,084, filed Nov. 19, 2021, which is pending.
U.S. Appl. No. 16/193,636, filed Nov. 16, 2018, which issued as U.S. Pat. No. 11,191,477 on Dec. 7, 2021.
U.S. Appl. No. 16/676,394, filed Nov. 6, 2019, which issued as U.S. Pat. No. 10,898,129 on Jan. 26, 2021.
U.S. Appl. No. 16/684,480, filed Nov. 14, 2019, which issued as U.S. Pat. No. 11,426,118 on Aug. 30, 2022.
Bluestein et al., "Pressure Ulcers: Prevention, Evalutaion, and Management," *Am. Fam. Physician,* 78(10):1186-1194 (Nov. 15, 2008), Herewith.
De Oliveira et al., "The accuracy of ultrasound, thermography, photography and sub-epidermal moisture as a predictor of pressure ulcer presence—a systematic review" unsigned thesis submitted to the School of Postgraduate Studies, Faculty of Medicine and Health Sciences, Royal College of Surgeons in Ireland, 316 pp. (2015), retrieved from http://pstorage-rcsi-9048708668.s3.amazonaws.com/19329779/Theaccuracyofultrasoundthermographyphotographyandsubepi.pdf, Herewith.
Extended European Search Report completed Jan. 1, 2025, in European Patent Application No. 22767802.6, Herewith.
Extended European Search Report completed Jan. 3, 2025, in European Patent Application No. 24214401.2, Herewith.
Extended European Search Report completed Feb. 3, 2025, in European Patent Application No. 24214403.8, Herewith.
National Institue for Health and Care Excellence ("NICE"), "Pressure Ulcers: Prevention and Management," *Clinical Guideline,* 11 pp. (Apr. 23, 2014), Herewith.
Reid et al., "Pressure Ulcer Prevention and Treatment: Use of Prophylactic Dressings" *Chronic Wound Care Management and Research,* 3:117-121 (Oct. 11, 2016), Herewith.
Stekelenburg et al., "Compression-Induced Tissue Damage: Animal Models," in *Pressure Ulcer Research,* Springer-Verlag, Berlin/Heidelberg, pp. 187-204 (Jan. 1, 2005), Herewith.
Vapiwala et al., "Enhancing Career Paths for Tomorrow's Radiation Oncologists," *International Journal of Radiation: Oncology Biology Physics,* 105(1):52-63 (May 22, 2019) (Pergamon Press), Herewith.
Great Britain Search Report dated Oct. 21, 2024, in Great Britain Patent Application No. GB2411677.4, Herewith.

* cited by examiner

| | CURRENT "DELTA" VALUE (COMPARED TO THRESHOLD VALUE "T") | | | | | | |
|---|---|---|---|---|---|---|---|
| | 0 | <T | T+m | T+2m | T+3m | ... | ≥T+S*m |
| 0 | 0 | 0 | 1 | 2 | 3 | ... | S |
| 1 | 0 | 1 | 2 | 3 | 4 | ... | S |
| 2 | 1 | 2 | 3 | 4 | 5 | ... | S |
| 3 | 2 | 3 | 4 | 5 | 6 | ... | S |
| 4 | 2 | 2 | 4 | 6 | 8 | ... | S |
| ... | ... | ... | ... | ... | ... | ... | ... |
| N | S-4 | S-2 | S-2 | S-1 | S | ... | S |

CURRENT LEVEL OF INTERVENTION — 502
506

PROVIDING A CONTINUITY OF CARE ACROSS MULTIPLE CARE SETTINGS

CROSS-REFERENCE TO RELATED APPLICATIONS

This application is a continuation of U.S. Non-Provisional application Ser. No. 16/193,707 filed Nov. 16, 2018, which claims benefit of U.S. Provisional Application No. 62/587,337, which was filed Nov. 16, 2017 and U.S. Provisional Application No. 62/693,810, which was filed Jul. 3, 2018. The entire content of these applications is incorporated herein by reference.

FIELD

The present disclosure provides methods of transferring and handling patient information, in particular information related to the risk of developing a pressure ulcer, to improve care when a patient receives care in multiple settings.

BACKGROUND

The skin is the largest organ in the human body. It is readily exposed to different kinds of damages and injuries. When the skin and its surrounding tissues are unable to redistribute external pressure and mechanical forces, ulcers may be formed. Prolonged continuous exposure to even modest pressure, such as the pressure created by the body weight of a supine patient on their posterior skin surfaces, may lead to a pressure ulcer. In the presence of other damage, such as the neuropathy and peripheral tissue weakening that can be induced by diabetes, even periodic exposure to moderate levels of pressure and stress may lead to an ulcer, for example a foot ulcer.

Pressure ulcers are developed by approximately 2.5 million people a year in the United States and an equivalent number in the European Union. In long-term and critical-care settings, up to 25% of elderly and immobile patients develop pressure ulcers. Approximately 60,000 U.S. patients die per year due to infection and other complications from pressure ulcers.

Detecting tissue damage before the skin breaks and intervening with the appropriate therapy to avoid further deterioration of the underlying tissue is desirable not only for the patient but society. The average cost of treating pressure-induced damage at the earliest visible sign (a Stage 1 ulcer) is only $2,000 but this rises to $129,000 when the ulcer is deep enough to expose muscle or bone (a Stage 4 ulcer.) Currently, patients normally receive universal prevention of pressure ulcers, meaning that the prevention does not target to any particular anatomical sites. Patients only receive a targeted, localized, treatment of ulcer after the pressure ulcer is developed to the point that it can be identified by a visual assessment. The current standard to detect pressure ulcers is by visual inspection, which is subjective, unreliable, untimely, and lacks specificity. Therefore, even when a patient is experiencing inflammation of the skin, a precursor of ulcer development, he or she would not be receiving a targeted, localized treatment for the developing ulcer. Instead, the inflammation would continue to develop into a full-blown ulcer.

In current practice, an independent assessment of a patient's risk of developing a pressure ulcer is performed upon arrive in a care setting. This lack of knowledge from the prior care setting may diminish the quality of care received at the new care setting.

SUMMARY

In one aspect, the present disclosure provides for, and includes, a method of identifying and providing an appropriate level of pressure ulcer care to a patient based on a plurality of Sub-Epidermal Moisture (SEM) measurements. In an aspect, a patient is provided with increasingly effective pressure ulcer interventions based on changes in SEM measurements. In an aspect, a patient is given less intensive pressure ulcer interventions based on changes in SEM measurements.

A method of providing a continuity of care for a patient during transfer between care settings, the method comprising the steps of: deciding to transfer a patient from a first care setting to a second care setting, performing a first assessment of the patient in the first care setting, preparing a transfer record of the assessment, and transferring the transfer record with the patient to the second care setting.

In an aspect, the present disclosure provides for, and includes, a method of identifying and treating a patient in need of pressure ulcer treatment, the method comprising the steps of: evaluating a patient for a risk of pressure ulcer in a patient upon admission to a care facility, where the evaluating step comprises making a first plurality of Sub-Epidermal Moisture (SEM) measurements in the patient, calculating a first delta value from a portion of the first plurality of SEM measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater. In a further aspect, the present disclosure provides for, and includes, making a second plurality of SEM measurements in the patient at a first pre-determined frequency corresponding to the administered intervention level, calculating a second delta value from a portion of the second plurality of SEM measurements, determining whether the second delta value exceeds a second threshold, continuing to administer the first intervention if the second delta value does not exceed the second threshold, continuing to make a plurality of SEM measurements at the first pre-determined frequency if the second delta value does not exceed the second threshold, administering a second intervention of level-M if the second delta value exceeds the second threshold, where M is an integer and M is greater than N, and making a plurality of SEM measurements at a second pre-determined frequency corresponding to level-M if the second delta value exceeds the second threshold. In yet a further aspect, the present disclosure provides for, and includes, determining whether the second delta value is less than a third threshold, administering a level-(N−1) intervention if the second delta value is less than the third threshold and if the first intervention is not of level-0, and making a plurality of SEM measurements at a pre-determined frequency corresponding to level-(N−1) if the second delta value is less than the third threshold.

In one aspect, the present disclosure provides for, and includes, a method of slowing the progression of pressure ulcer development in a patient in need thereof, the method comprising the steps of: identifying a current intervention of level-K received by the patient, making a plurality of Sub-Epidermal Moisture (SEM) measurements in the patient, calculating a delta value from a portion of the plurality of SEM measurements, determining whether the delta value exceeds a first threshold, continuing to administer the current intervention if the delta value does not exceed the first threshold, continuing to make a plurality of SEM measurements at a pre-determined frequency corresponding to level-K if the delta value does not exceed the first threshold, administering a new intervention of level-N if the delta value exceeds the first threshold, where N has a value greater than K, and making a plurality of SEM measurements at a pre-determined frequency corresponding to level-N if the delta value exceeds the first threshold. In a further aspect, the present disclosure provides for, and includes, determining whether the delta value is less than a second threshold, administering a level-L intervention if the delta value is less than the second threshold, where L has a non-negative value less than K, and making a plurality of SEM measurements at a pre-determined frequency corresponding to level-L if the delta value is less than the second threshold.

In an aspect, the present disclosure provides for, and includes, a method of stratifying groups of patients in a care facility based on pressure ulcer risk, the method comprising the steps of: making a plurality of Sub-Epidermal Moisture (SEM) measurements in each of the patients, calculating a delta value from a portion of the plurality of SEM measurements for each of the patients, determining whether each delta value exceeds any values in a set of threshold values corresponding to N care levels and assigning a care level to each of the patients, rearranging the group of patients based on each of the patient's assigned care levels.

In one aspect, the present disclosure provides for, and includes, a method of reducing incidence of pressure ulcer in patients admitted to a care facility, the method comprising the steps of: evaluating a patient for a risk of pressure ulcer upon admission to the care facility, where the evaluating step comprises making a first plurality of Sub-Epidermal Moisture (SEM) measurements in the patient, calculating a first delta value from a portion of the first plurality of SEM measurements, determining whether the first delta value exceeds a first threshold, administering a first intervention of level-0 if the first delta value does not exceed the first threshold, and administering a & intervention of level-N if the first delta value exceeds the first threshold, where N is an integer and N has a value of 1 or greater.

In an aspect, the present disclosure provides for, and includes, a method of identifying and treating a patient in need of application of a barrier cream to the patient's heel, the method comprising the steps of: making a plurality of Sub-Epidermal Moisture (SEM) measurements at the patient's heel, calculating a delta value from a portion of the plurality of SEM measurements, determining whether the delta value exceeds a threshold corresponding to level N, where N is greater than or equal to 2, administering a barrier cream to the patient's heel if the delta value exceeds the threshold, and making a plurality of SEM measurements every two hours if the delta value exceeds the threshold.

In one aspect, the present disclosure provides for, and includes, a method of identifying and treating a patient in need of application of a neuro-muscular stimulation to the patient's heel, the method comprising the steps of: making a plurality of Sub-Epidermal Moisture (SEM) measurements at the patient's heel, calculating a delta value from a portion of the plurality of SEM measurements, determining whether the delta value exceeds a threshold corresponding to level N, where N is greater than or equal to 2, administering a neuro-muscular stimulation to the patient's heel if the delta value exceeds the threshold, and making a plurality of SEM measurements every hour if the delta value exceeds the threshold.

In an aspect, the present disclosure provides for, and includes, a method of identifying and treating a patient in need of application of a topical cream to the patient's heel, the method comprising the steps of: making a plurality of Sub-Epidermal Moisture (SEM) measurements at the patient's heel, calculating a delta value from a portion of the plurality of SEM measurements, determining whether the delta value exceeds a threshold corresponding to level N, where N is greater than or equal to 2, administering a topical cream to the patient's heel if the delta value exceeds the threshold, and making a plurality of SEM measurements every half an hour if the delta value exceeds the threshold.

In one aspect, the present disclosure provides for, and includes, a method of identifying and treating a patient in need of application of a barrier cream to the patient's sacrum, the method comprising the steps of: making a plurality of Sub-Epidermal Moisture (SEM) measurements at the patient's sacrum, calculating a delta value from a portion of the plurality of SEM measurements, determining whether the delta value exceeds a threshold corresponding to level N, where N is greater than or equal to 2, administering a barrier cream to the patient's sacrum if the delta value exceeds the threshold, and making a plurality of SEM measurements every six hours if the delta value exceeds the threshold.

In an aspect, the present disclosure provides for, and includes, a method of identifying and treating a patient in need of application of a neuro-muscular stimulation to the patient's sacrum, the method comprising the steps of: making a plurality of Sub-Epidermal Moisture (SEM) measurements at the patient's sacrum, calculating a delta value from a portion of the plurality of SEM measurements, determining whether the delta value exceeds a threshold corresponding to level N, where N is greater than or equal to 2, administering a neuro-muscular stimulation to the patient's sacrum if the delta value exceeds the threshold, and making a plurality of SEM measurements every four hours if the delta value exceeds the threshold.

In one aspect, the present disclosure provides for, and includes, a method of identifying and treating a patient in need of application of a topical cream to the patient's sacrum, the method comprising the steps of: making a plurality of Sub-Epidermal Moisture (SEM) measurements at the patient's sacrum, calculating a delta value from a portion of the plurality of SEM measurements, determining whether the delta value exceeds a threshold corresponding to level N, where N is greater than or equal to 2, administering a topical cream to the patient's sacrum if the delta value exceeds the threshold, and making a plurality of SEM measurements every two hours if the delta value exceeds the threshold.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

FIG. 5 is an example of a workflow guidance matrix where the current level of intervention and the new delta value are used to select the new level of intervention in accordance with the present disclosure.

FIGS. 6A, 6B, and 6C depict an example progression over time of a delta value for a single patient at a single location where a pressure ulcer develops in accordance with the present disclosure.

DETAILED DESCRIPTION

Figure 1:
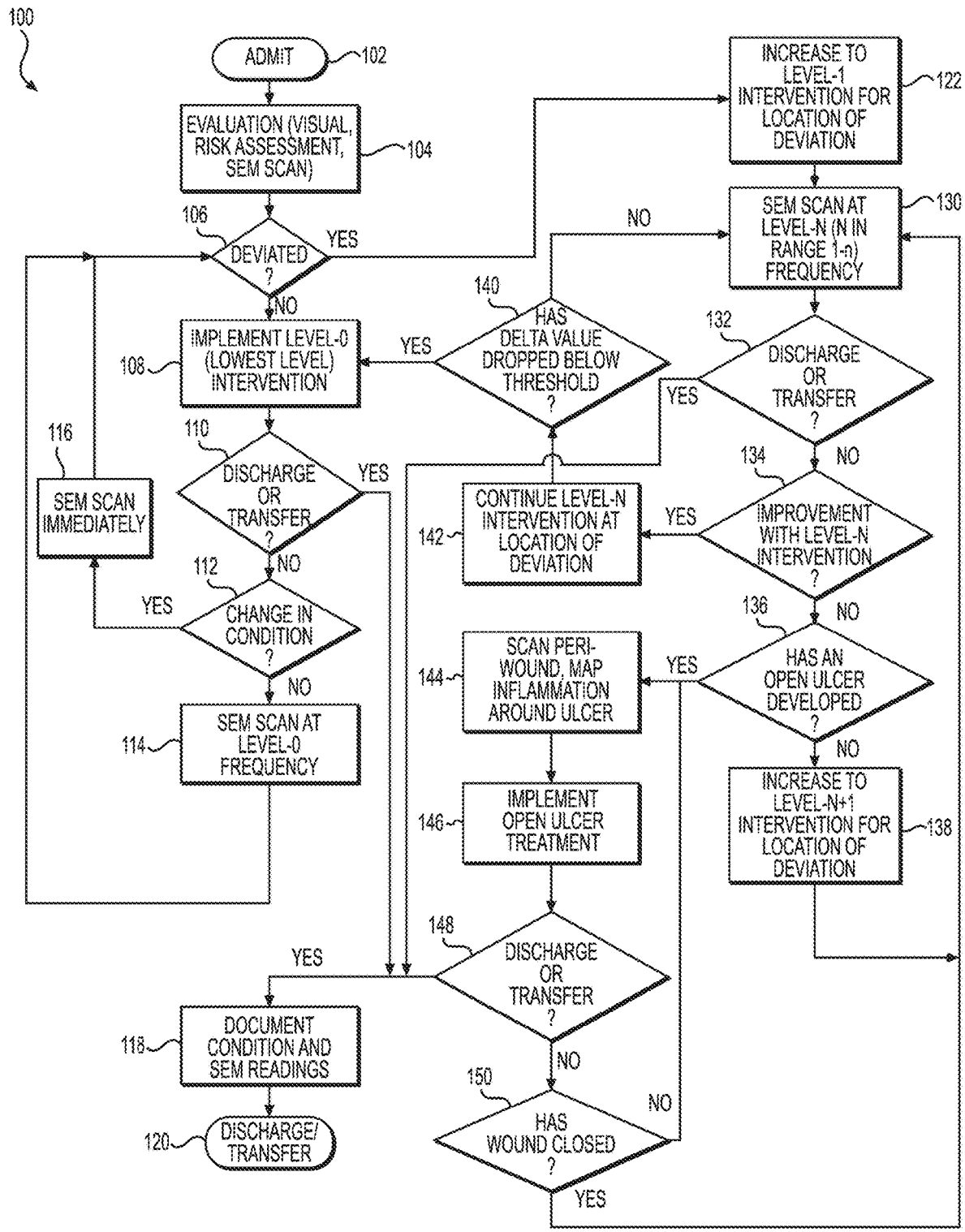
FIG. 1 depicts an example of an overall process for selecting a pressure ulcer treatment based on SEM values from admission to a care facility until discharge from the care facility, in accordance with the present disclosure.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

U.S. patent application Ser. No. 14/827,375 ("the '375 application") discloses an apparatus that uses radio frequency (RF) energy to measure the sub-epidermal capacitance using a bipolar sensor, where the sub-epidermal capacitance corresponds to the moisture content of the target region of skin of a patient. The '375 application also discloses an array of these bipolar sensors of various sizes.

U.S. patent application Ser. No. 15/134,110 discloses an apparatus for measuring sub-epidermal moisture (SEM) similar to the device shown in FIG. 3, where the device emits and receives an RF signal at a frequency of 32 kHz through a single coaxial sensor and generates a bioimpedance signal, then converts this signal to a SEM value.

Both U.S. patent application Ser. Nos. 14/827,375 and 15/134,110 are incorporated herein by reference in their entireties. However, the SEM values of this application may be measured by any similar or equivalent devices or techniques that would be apparent to one of skill in the art. For example, a device measuring the SEM values of this application may be a wired device, a wireless device, or a system comprising various components in communication with each other.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an," and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "sub-epidermal moisture" or "SEM" refers to the increase in tissue fluid and local edema caused by vascular leakiness and other changes that modify the underlying structure of the damaged tissue in the presence of continued pressure on tissue, apoptosis, necrosis, and the inflammatory process.

As used herein, a "patient" may be a human or animal subject.

As used herein, "delta" refers to a calculated difference between two SEM values.

As used herein, the variables "K," "L," "M," and "N" are non-negative integers.

FIG. 1 depicts an overall process 100 for selecting a pressure ulcer treatment based on SEM values produced from SEM measurements made using an SEM scanner in accordance with this disclosure, from admission to a care facility until discharge from the care facility. In an aspect, a care facility is selected from the group consisting of a hospital, an assisted living facility, a residential care facility, a nursing home, a long-term care facility, a continuing care community, and an independent living community. In an aspect, a care facility may be a home or other residence of the patient, whereupon the "admit" step 102 will be a first evaluation of a patient at their home by a nurse or other caregiver. In one aspect, the schedule of interventions and evaluation intervals used in a home setting may be different than the corresponding interventions and intervals used at a hospital.

In an aspect, in process 100, a newly admitted patient receives an intake evaluation in step 104 that includes one or more of a visual examination of a portion of the patient's skin, completion of at least a portion of a risk assessment protocol that evaluates one or more of nutrition, mobility, physical activity, physical strength, and ability to communicate, and SEM measurements made in one or more locations on the patient's skin. In an aspect, the SEM measurements may include making a plurality of SEM measurements at a single "location" on the patient's skin. In one aspect, "location" is considered as an area rather than a single point such that SEM measurements may be made at spatially separated points within the location. For example, a "heel" location includes the medial, lateral, and posterior surfaces around the heel as well as the posterior portion of the sole of that foot.

In one aspect, once the evaluation step is complete, a determination is made in step 106 as to whether the patient is "deviated," i.e., whether the combination of the results of the various elements of the evaluation indicate that the patient has, or is at risk of developing, tissue damage that could lead to a pressure ulcer. Each element of the evaluation may have an individual criterion for level of risk, for example a scoring system with threshold value that indicates an unacceptable risk. In an aspect, there is a protocol to combine the criteria to generate a composite parameter that can be used to select a level of intervention.

In an aspect, if the patient is determined to be at an acceptable level of risk, the process branches to step 108 which implements the lowest level of intervention, designated herein as "level-zero" or "level-0." Progressing through steps 110 and 112, the patient will be re-assessed using at least the SEM measurement protocol in step 114 at a frequency, or conversely a time interval, associated with level-0. The process 100 then loops back to step 106 to evaluate the results of the SEM measurements made in step 114.

In one aspect, if the patient is determined in step 106 to be deviated, then the process branches to step 122, which implements a higher level of intervention. In an aspect, there is a defined hierarchy of intervention levels, with each level implementing a more effective intervention than the next-lower level. In an aspect, each level also has a defined monitoring interval or frequency indicating how often a set of SEM measurements should be made, where higher levels will generally have shorter intervals. In this example, the process has been defined by the hospital, or other administering organization, to step up one level to a level-1 intervention at this point. In another aspect, step 122 may implement a level-2 or higher level of intervention. The process now enters a new loop starting at step 130 where the patient will now be monitored at a level-N frequency where N is in the range of 1 to n, n being the highest defined level of intervention and monitoring.

In an aspect, at step 134, the patient's history is evaluated to determine whether their condition is improving. If the patient's condition is improving, for example as evidenced by a decreasing delta value, then the process branches to step 142. In this example, step 142 continues to implement the current level of intervention and the process loops through step 140 to steps 130-132-134-142-140 until the delta value drops below the threshold. In an aspect, the level of intervention may be reduced in step 142 based on the magnitude of the delta value as the delta value trends downward.

In one aspect, if the patient does not show improvement in step 134, the process branches to an increase in the level of intervention in step 138 provided that the skin is not broken, i.e., an open ulcer has not developed, in step 136. If an open ulcer has developed, the SEM scanning will now be performed around the periphery of the open wound in step 144 to map inflammation or other precursor indication of ulcer spreading. The ulcer itself is treated in step 148 and this secondary loop 144-146-148-150 continues until the wound closes, whereupon the process returns to step 130.

In an aspect, at any time in process 100, discharge of the patient branches to step 118, where the condition of the patient upon discharge or transfer is documented. In an aspect, step 118 comprises a final set of SEM measurements at one of more locations on the patient's body. In an aspect, these locations include areas that were not receiving an intervention and were not previously identified as at risk. In an aspect, this information is provided to the receiving caregiver. The patient is then discharged or transferred in step 120.

In an aspect, the present disclosure provides for, and includes, a method of identifying and treating a patient in need of pressure ulcer treatment, the method comprising the steps of: evaluating a patient for a risk of pressure ulcer in a patient upon admission to a care facility, where the evaluating step comprises making a first plurality of Sub-Epidermal Moisture (SEM) measurements in the patient, calculating a first delta value from a portion of the first plurality of SEM measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater.

In one aspect, a first plurality of SEM measurements is taken at and around one or more anatomical sites selected from the group consisting of a sternum, a sacrum, a heel, a scapula, an elbow, an ear, and other fleshy tissues of a patient. In an aspect, a first plurality of SEM measurements is separated into sub-groups for analysis based on the general location at which a measurement is taken. In one aspect, a first plurality of SEM measurements is taken at locations located on one or more concentric circles centered around an anatomical site. In an aspect, a first plurality of SEM measurements is taken at locations located on a straight line at approximately equidistance from an anatomical site.

In one aspect, a first delta value is determined by the difference between the maximum SEM value and the minimum SEM value from the first plurality of SEM measurements collected. In an aspect, a first delta value is determined by the difference between the maximum SEM average of measurements taken at one location and the minimum SEM average of measurements taken at a second location. In one aspect, a first delta value is determined for a portion of a first plurality of SEM measurements made up of a sub-group as defined by location taken. In an aspect, an average SEM value at a location is obtained from two, three, four, five, six, seven, eight, nine, ten, or more than ten SEM values measured at that location. In one aspect, a first delta value is determined by the difference between SEM values derived from measurements taken at two bisymmetric locations with respect to a centerline.

In an aspect, a delta value may be calculated from a plurality of SEM measurements made at a certain location, or in close proximity around a specific location, in a plurality of methods. In an aspect, a plurality of SEM measurements are made in a pre-determined pattern on the skin and the delta value is calculated by subtracting the SEM value associated with a pre-determined position within the pattern from the largest SEM value made at the other positions in the pattern. In an aspect, a plurality of SEM measurements are made in a pre-determined pattern on the skin and the delta value is calculated by identifying the SEM value associated with a pre-determined position within the pattern and subtracting the largest SEM value made at the other positions in the pattern. In an aspect, an average SEM value may be calculated from a portion of a set of SEM values generated by a plurality of SEM measurements at a single location and a delta value calculated as the largest difference between the average and a single SEM value of the same set. In an aspect, a delta value may be calculated as a ratio of the largest SEM value to the smallest SEM value within a set of SEM values.

In an aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a first threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a first threshold can be scaled by a factor or a multiple based on the values provided herein. It will be understood that a threshold is not limited by design, but rather, one of ordinary skill in the art would be capable of choosing a predetermined value based on a given unit of SEM. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, N ranges from 1 to 50, such as from 1 to 2, from 1 to 3, from 1 to 4, from 1 to 5, from 1 to 6, from 1 to 7, from 1 to 8, from 1 to 9, from 1 to 10, from 1 to 15, from 1 to 20, from 1 to 25, from 1 to 30, from 1 to 35, from 1 to 40, or from 1 to 45.

In one aspect, N is determined by the amount by which the first delta value exceeds the first threshold. In an aspect, the amount by which a delta value exceeds a threshold established for (N+1) is greater than the amount by which a delta value exceeds a threshold established for N. In one aspect, the amount by which a delta value exceeds a threshold established for (N−1) is less than the amount by which a delta value exceeds a threshold established for N.

In an aspect, a level-1 (N=1) intervention is applied to a patient having a delta value exceeding the threshold by not more than 100% of the threshold value, such as not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In an aspect, a level-2 (N=2) intervention is applied to a patient having a delta value exceeding the threshold by not more than 150% of the threshold value, such as not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-3 (N=3) intervention is applied to a patient having a delta value exceeding the threshold by not more than 200% of the threshold value, such as not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-4 (N=4) intervention is applied to a patient having a delta value exceeding the threshold by not more than 250% of the threshold value, such as not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-5 (N=5) intervention is applied to a patient having a delta value exceeding the threshold by not more than 300% of the threshold value, such as not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-6 (N=6) intervention is applied to a patient having a delta value exceeding the threshold by not more than 350% of the threshold value, such as not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-7 (N=7) intervention is applied to a patient having a delta value exceeding the threshold by not more than 400% of the threshold value, such as not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-8 (N=8) intervention is applied to a patient having a delta value exceeding the threshold by not more than 450% of the threshold value, such as not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-9 (N=9) intervention is applied to a patient having a delta value exceeding the threshold by not more than 500% of the threshold value, such as not more than 495%, not more than 490%, not more than 485%, not more than 480%, not more than 475%, not more than 470%, not more than 465%, not more than 460%, not more than 455%, not more than 450%, not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-10 (N=10) intervention is applied to a patient having a delta value exceeding the threshold by not more than 550% of the threshold value, such as not more than 545%, not more than 540%, not more than 535%, not more than 530%, not more than 525%, not more than 520%, not more than 515%, not more than 510%, not more than 505%, not more than 500%, not more than 495%, not more than 490%, not more than 485%, not more than 480%, not more than 475%, not more than 470%, not more than 465%, not more than 460%, not more than 455%, not more than 450%, not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value.

In one aspect, a level-N intervention is more effective than a level-0 intervention. In an aspect, a level-(N+1) intervention is more effective than a level-N intervention. In one aspect, a level-(N−1) intervention is less effective than a level-N intervention.

In an aspect, the evaluating step of the present disclosure further comprises performing a visual assessment. In one aspect, the visual assessment is performed in accordance with the guidelines of the National Pressure Ulcer Advisory Panel (NPUAP).

In one aspect, the evaluating step of the present disclosure further comprises performing a risk assessment. In an aspect, the risk assessment is performed in accordance with a test selected from the group consisting of the Braden Scale, the Gosnell Scale, the Norton Scale, and the Waterlow Scale.

In an aspect, the present disclosure further provides for, and includes, making a second plurality of SEM measurements in the patient at a first pre-determined frequency corresponding to the administered intervention level, calculating a second delta value from a portion of the second plurality of SEM measurements, determining whether the second delta value exceeds a second threshold, continuing to administer the first intervention if the second delta value does not exceed the second threshold, continuing to make a plurality of SEM measurements at the first pre-determined frequency if the second delta value does not exceed the second threshold, administering a second intervention of level-M if the second delta value exceeds the second threshold, where M is an integer and M is greater than N, and making a plurality of SEM measurements at a second pre-determined frequency corresponding to level-M if the second delta value exceeds the second threshold.

In one aspect, a pre-determined frequency is selected from the group consisting of at least once every 72 hours, at least once every 48 hours, at least once every 24 hours, at least once every 12 hours, at least once every 8 hours, at least once every 6 hours, at least once every 4 hours, at least once every 3 hours, at least once every 2 hours, at least once every hour, and at least once every half an hour.

In one aspect, a second plurality of SEM measurements are taken in accordance with.

In an aspect, a second plurality of SEM measurements are made at the same locations where a first plurality of SEM measurements were taken. In one aspect, a second plurality of SEM measurements are made at some of the same locations where a first plurality of SEM measurements were taken. In an aspect, a second plurality of SEM measurements are made near the locations where a first plurality of SEM measurements were taken. In one aspect, a second plurality of SEM measurements are made at different locations than where a first plurality of SEM measurements were taken.

In an aspect, a second delta value is determined by the difference between the maximum SEM value and the minimum SEM value from the second plurality of SEM measurements collected. In one aspect, a second delta value is determined by the difference between the maximum SEM average of measurements taken at one location and the minimum SEM average of measurements taken at a second location. In one aspect, a second delta value is determined for a portion of a second plurality of SEM measurements made up of a sub-group as defined by location taken.

In an aspect, a second threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a second threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a second threshold can be scaled by a factor or a multiple based on the values provided herein. In one aspect, a second threshold can be the same as a first threshold. In an aspect, a second threshold can be greater than a first threshold. In one aspect, a second threshold can be less than a first threshold.

In an aspect, M ranges from 2 to 50, such as from 2 to 3, from 2 to 4, from 2 to 5, from 2 to 6, from 2 to 7, from 2 to 8, from 2 to 9, from 2 to 10, from 2 to 15, from 2 to 20, from 2 to 25, from 2 to 30, from 2 to 35, from 2 to 40, or from 2 to 45.

In one aspect, M is determined by the amount by which the second delta value exceeds the second threshold. In an aspect, the amount by which a delta value exceeds a threshold established for (M+1) is greater than the amount by which a delta value exceeds a threshold established for M. In one aspect, the amount by which a delta value exceeds a threshold established for (M−1) is less than the amount by which a delta value exceeds a threshold established for M.

In an aspect, a level M intervention is chosen in accordance with [0063] to [0072], replacing N with M.

In one aspect, the present disclosure further provides for, and includes, determining whether the second delta value is less than a third threshold, administering a level-(N−1) intervention if the second delta value is less than the third threshold and if the first intervention is not of level-0, and making a plurality of SEM measurements at a pre-determined frequency corresponding to level-(N−1) if the second delta value is less than the third threshold.

In an aspect, a third threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a third threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a third threshold can be scaled by a factor or a multiple based on the values provided herein. In one aspect, a third threshold can be the same as a second threshold. In an aspect, a third threshold can be greater than a second threshold. In one aspect, a third threshold can be less than a second threshold. In one aspect, a third threshold can be the same as a first threshold. In an aspect, a third threshold can be greater than a first threshold. In one aspect, a third threshold can be less than a first threshold.

In an aspect, a second delta value can be 0.1-99.5% of the third threshold, such as 0.1-1%, 0.1-5%, 1-5%, 5-15%, 10-20%, 15-25%, 20-30%, 25-35%, 30-40%, 35-45%, 40-50%, 0.1-25%, 15-35%, 25-50%, 25-75%, 45-55%, 50-60%, 55-65%, 60-70%, 65-75%, 40-55%, 50-75%, 50-99.5%, 70-80%, 75%-85%, 80-90%, 85-95%, 90-99.5%, 65-85%, or 75-99.5% of the third threshold.

In one aspect, the present disclosure provides for, and includes, a method of slowing the progression of pressure ulcer development in a patient in need thereof, the method comprising the steps of: identifying a current intervention of level-K received by the patient, making a plurality of Sub-Epidermal Moisture (SEM) measurements in the patient, calculating a delta value from a portion of the plurality of SEM measurements, determining whether the delta value exceeds a first threshold, continuing to administer the current intervention if the delta value does not exceed the first threshold, continuing to make a plurality of SEM measurements at a pre-determined frequency corresponding to level-K if the delta value does not exceed the first threshold, administering a new intervention of level-N if the delta value exceeds the first threshold, where N has a value greater than K, and making a plurality of SEM measurements at a pre-determined frequency corresponding to level-N if the delta value exceeds the first threshold. In an aspect, a patient in need thereof is a patient experiencing a change of care, a change in mobility, a change in nutrition, a change in sensory perception, or a combination thereof. In one aspect, a patient in need thereof is a patient having developed an open ulcer. In an aspect, a patient in need thereof is a patient having recovered from an open ulcer. In one aspect, a patient in need thereof is a patient receiving surgery. In an aspect, a patient in need thereof is a patient receiving spinal analgesics or sacral analgesics during a surgery. In one aspect, a patient in need thereof is a patient receiving a surgery for a duration of four or more hours, such as five or more hours, six or more hours, seven or more hours, eight or more hours, nine or more hours, ten or more hours, eleven or more hours, or twelve or more hours. In an aspect, a surgery has a duration of one or more hours, such as two or more hours, or three or more hours.

In one aspect, a plurality of SEM measurements are taken in accordance with [0057]. In an aspect, a delta value is determined in accordance with [0058]. In one aspect, a first threshold is determined in accordance with [0060].

In an aspect, K ranges from 2 to 50, such as from 2 to 3, from 2 to 4, from 2 to 5, from 2 to 6, from 2 to 7, from 2 to 8, from 2 to 9, from 2 to 10, from 2 to 15, from 2 to 20, from 2 to 25, from 2 to 30, from 2 to 35, from 2 to 40, or from 2 to 45.

In an aspect, K is determined by the amount by which the delta value exceeds the threshold. In an aspect, the amount by which a delta value exceeds a threshold established for (K+1) is greater than the amount by which a delta value exceeds a threshold established for K. In one aspect, the amount by which a delta value exceeds a threshold established for (K−1) is less than the amount by which a delta value exceeds a threshold established for K.

In an aspect, a level K intervention is chosen in accordance with [0063] to [0072], replacing N with K.

In an aspect, the present disclosure further provides for, and includes, determining whether the delta value is less than a second threshold, administering a level-L intervention if the delta value is less than the second threshold, where L has a non-negative value less than K, and making a plurality of SEM measurements at a pre-determined frequency corresponding to level-L if the delta value is less than the second threshold.

In an aspect, a second threshold is determined in accordance with [0080].

In an aspect, L can be K−1, K−2, K−3, K−4, K−5, K−6, K−7, K−8, K−9, or K−10. In one aspect, L is K−1 if a delta value is 90-99.5% of the second threshold, such as 90-95%, 91-96%, 92-97%, 93-98%, 94-99%, or 95-99.5% of the second threshold, unless K−1 is less than 0, in which case L would be 0. In an aspect, L is K−2 if a delta value is 80-89.9% of the second threshold, such as 80-85%, 81-86%, 82-87%, 83-88%, 84-89%, or 85-89.9% of the second threshold, unless K−2 is less than 0, in which case L would be 0. In one aspect, L is K−3 if a delta value is 70-79.9% of the second threshold, such as 70-75%, 71-76%, 72-77%, 73-78%, 74-79%, or 75-79.9% of the second threshold, unless K−3 is less than 0, in which case L would be 0. In an aspect, L is K−4 if a delta value is 60-69.9% of the second threshold, such as 60-65%, 61-66%, 62-67%, 63-68%, 64-69%, or 65-69.9% of the second threshold, unless K−4 is less than 0, in which case L would be 0. In one aspect, L is K−5 if a delta value is 50-59.9% of the second threshold, such as 50-55%, 51-56%, 52-57%, 53-58%, 54-59%, or 55-59.9% of the second threshold, unless K−5 is less than 0, in which case L would be 0. In an aspect, L is K−6 if a delta value is 40-49.9% of the second threshold, such as 40-45%, 41-46%, 42-47%, 43-48%, 44-49%, or 45-49.9% of the second threshold, unless K−6 is less than 0, in which case L would be 0. In one aspect, L is K−7 if a delta value is 30-39.9% of the second threshold, such as 30-35%, 31-36%, 32-37%, 33-38%, 34-39%, or 35-39.9% of the second threshold, unless K−7 is less than 0, in which case L would be 0. In an aspect, L is K−8 if a delta value is 20-29.9% of the second threshold, such as 20-25%, 21-26%, 22-27%, 23-28%, 24-29%, or 25-29.9% of the second threshold, unless K−8 is less than 0, in which case L would be 0. In one aspect, L is K−9 if a delta value is 10-19.9% of the second threshold, such as 10-15%, 11-16%, 12-17%, 13-18%, 14-19%, or 15-19.9% of the second threshold, unless K−9 is less than 0, in which case L would be 0. In an aspect, L is K−10 if a delta value is 0.1-9.9% of the second threshold, such as 0.1-5%, 1-6%, 2-7%, 3-8%, 4-9%, or 5-9.9% of the second threshold, unless K−10 is less than 0, in which case L would be 0.

In an aspect, the present disclosure provides for, and includes, a method of stratifying groups of patients in a care facility based on pressure ulcer risk, the method comprising the steps of: making a plurality of Sub-Epidermal Moisture (SEM) measurements in each of the patients, calculating a delta value from a portion of the plurality of SEM measurements for each of the patients, determining whether each delta value exceeds any values in a set of threshold values corresponding to N care levels and assigning a care level to each of the patients, rearranging the group of patients based on each of the patient's assigned care levels.

In one aspect, the present disclosure provides for, and includes, a method of reducing incidence of pressure ulcer in patients admitted to a care facility, the method comprising the steps of: evaluating a patient for a risk of pressure ulcer upon admission to the care facility, where the evaluating step comprises making a first plurality of Sub-Epidermal Moisture (SEM) measurements in the patient, calculating a first delta value from a portion of the first plurality of SEM measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater. In an aspect, the incidence of ulcers in patients in the care facility is reduced to less than 1 in 100, less than 1 in 200, less than 1 in 300, less than 1 in 400, less than 1 in 500, less than 1 in 600, less than 1 in 700, less than 1 in 800, less than 1 in 900, or less than 1 in 1000.

In an aspect, the present disclosure provides for, and includes, a method of identifying and treating a patient in need of application of a barrier cream to the patient's heel, the method comprising the steps of: making a plurality of Sub-Epidermal Moisture (SEM) measurements at the patient's heel, calculating a delta value from a portion of the plurality of SEM measurements, determining whether the delta value exceeds a threshold corresponding to level N, where N is greater than or equal to 2, administering a barrier cream to the patient's heel if the delta value exceeds the threshold, and making a plurality of SEM measurements every two hours if the delta value exceeds the threshold. In an aspect, a plurality of SEM measurements are made at least once every hour or at least once every half an hour if the delta value exceeds the threshold.

In one aspect, the present disclosure provides for, and includes, a method of identifying and treating a patient in need of application of a neuro-muscular stimulation to the patient's heel, the method comprising the steps of: making a plurality of Sub-Epidermal Moisture (SEM) measurements at the patient's heel, calculating a delta value from a portion of the plurality of SEM measurements, determining whether the delta value exceeds a threshold corresponding to level N, where N is greater than or equal to 2, administering a neuro-muscular stimulation to the patient's heel if the delta value exceeds the threshold, and making a plurality of SEM measurements every hour if the delta value exceeds the threshold. In an aspect, a plurality of SEM measurements are made at least once every half an hour if the delta value exceeds the threshold.

In an aspect, the present disclosure provides for, and includes, a method of identifying and treating a patient in need of application of a topical cream to the patient's heel, the method comprising the steps of: making a plurality of Sub-Epidermal Moisture (SEM) measurements at the patient's heel, calculating a delta value from a portion of the plurality of SEM measurements, determining whether the delta value exceeds a threshold corresponding to level N, where N is greater than or equal to 2, administering a topical cream to the patient's heel if the delta value exceeds the threshold, and making a plurality of SEM measurements every half an hour if the delta value exceeds the threshold.

In one aspect, the present disclosure provides for, and includes, a method of identifying and treating a patient in need of application of a barrier cream to the patient's sacrum, the method comprising the steps of: making a plurality of Sub-Epidermal Moisture (SEM) measurements at the patient's sacrum, calculating a delta value from a portion of the plurality of SEM measurements, determining whether the delta value exceeds a threshold corresponding to level N, where N is greater than or equal to 2, administering a barrier cream to the patient's sacrum if the delta value exceeds the threshold, and making a plurality of SEM measurements every six hours if the delta value exceeds the threshold. In an aspect, a plurality of SEM measurements are made at least once every four hours, at least once every three hours, at least once every two hours, at least once an hour, or at least once every half an hour if the delta value exceeds the threshold.

In an aspect, the present disclosure provides for, and includes, a method of identifying and treating a patient in need of application of a neuro-muscular stimulation to the patient's sacrum, the method comprising the steps of: making a plurality of Sub-Epidermal Moisture (SEM) measurements at the patient's sacrum, calculating a delta value from a portion of the plurality of SEM measurements, determining whether the delta value exceeds a threshold corresponding to level N, where N is greater than or equal to 2, administering a neuro-muscular stimulation to the patient's sacrum if the delta value exceeds the threshold, and making a plurality of SEM measurements every four hours if the delta value exceeds the threshold. In an aspect, a plurality of SEM measurements are made at least once every three hours, at least once every two hours, at least once an hour, or at least once every half an hour if the delta value exceeds the threshold.

In one aspect, the present disclosure provides for, and includes, a method of identifying and treating a patient in need of application of a topical cream to the patient's sacrum, the method comprising the steps of: making a plurality of Sub-Epidermal Moisture (SEM) measurements at the patient's sacrum, calculating a delta value from a portion of the plurality of SEM measurements, determining whether the delta value exceeds a threshold corresponding to level N, where N is greater than or equal to 2, administering a topical cream to the patient's sacrum if the delta value exceeds the threshold, and making a plurality of SEM measurements every two hours if the delta value exceeds the threshold. In an aspect, a plurality of SEM measurements are made at least once an hour or at least once every half an hour if the delta value exceeds the threshold.

In an aspect, methods of the present disclosure are performed using the devices disclosed in U.S. application Ser. Nos. 14/827,375 and 15/134,110. In one aspect, the moisture content is equivalent to the SEM value on a predetermined scale. In an aspect, a predetermined scale may range from 0 to 20, such as from 0 to 1, from 0 to 2, from 0 to 3, from 0 to 4, from 0 to 5, from 0 to 6, from 0 to 7, from 0 to 8, from 0 to 9, from 0 to 10, from 0 to 11, from 0 to 12, from 0 to 13, from 0 to 14, from 0 to 15, from 0 to 16, from 0 to 17, from 0 to 18, from 0 to 19. In one aspect, a predetermined scale can be scaled by a factor or a multiple based on the values provided herein.

In an aspect, the present disclosure further provides for, and includes, providing targeted treatment to an anatomical location of a patient identified as being damaged by a combination of a visual assessment and SEM scan measurements. In one aspect, a targeted treatment is provided to a common site for pressure ulcers selected from the group consisting of: toes, heels, a sacrum, a spine, an elbows, shoulder blades, occiput, and ischial tuberosity. In an aspect, a targeted treatment is concurrently provided to a second common site for pressure ulcers selected from the group consisting of: toes, heels, a sacrum, a spine, an elbows, shoulder blades, occiput, and ischial tuberosity. In one aspect, a first site receiving a targeted treatment is known to cause a development of pressure ulcer at a second site.

The present disclosure is illustrated by the following examples. The examples set out herein illustrate several aspects of the present disclosure but should not be construed as limiting the scope of the present disclosure in any manner.

EXAMPLES

Example 1: Intervention Levels for Treating Pressure Ulcers in the Heel

Subjects identified as being at risk for pressure ulcers in the heel were treated in accordance with the following scheme:

TABLE 1

EXAMPLE INTERVENTION SCHEME FOR TREATING PRESSURE ULCER IN THE HEEL

| Risk Level | Intervention | Frequency of Subsequent SEM Measurement Monitoring | Corresponding SEM delta Ranges |
|---|---|---|---|
| 0 | provide good nutrition, standard mattress, and/or turn every 24 hours | every 24 hours | SEM delta ≤ threshold |
| 1 | provide a heel boot | every 10 hours | threshold < SEM delta ≤ 105% threshold |
| 2 | change of support surface | at the beginning of each nursing shift | 105% threshold < SEM delta ≤ 110% threshold |
| 3 | apply dressing to back or sides of heel | every 12 hours | 110% threshold < SEM delta ≤ 115% threshold |
| 4 | change to low-friction sheet cover | every 8 hours | 115% threshold < SEM delta ≤ 120% threshold |
| 5 | provide a low-friction padded mattress surface for lower leg | every 6 hours | 120% threshold < SEM delta ≤ 125% threshold |
| 6 | turn patient at a shorter interval | every 4 hours | 125% threshold < SEM delta ≤ 130% threshold |
| 7 | apply barrier cream | every 2 hours | 130% threshold < SEM delta ≤ 135% threshold |

TABLE 1-continued

EXAMPLE INTERVENTION SCHEME FOR
TREATING PRESSURE ULCER IN THE HEEL

| Risk Level | Intervention | Frequency of Subsequent SEM Measurement Monitoring | Corresponding SEM delta Ranges |
|---|---|---|---|
| 8 | apply neuro-muscular stimulation | every 1 hour | 135% threshold < SEM delta ≤ 145% threshold |
| 9 | apply topical cream to enhance perfusion | every 30 minutes | 145% threshold < SEM delta ≤ 150% threshold |
| 10 | provide silicone pad for lower leg | every 15 minutes | 150% threshold < SEM delta |

Example 2: Intervention Levels for Treating Pressure Ulcers in the Sacrum

Subjects identified as being at risk for pressure ulcers in the sacrum were treated in accordance with the following scheme:

TABLE 2

EXAMPLE INTERVENTION SCHEME FOR
TREATING PRESSURE ULCER IN THE SACRUM

| Risk Level | Intervention | Frequency of Subsequent SEM Measurement Monitoring | Corresponding SEM delta Ranges |
|---|---|---|---|
| 0 | provide good nutrition, standard mattress, and/or turn every 24 hours | every 24 hours | SEM delta ≤ threshold |
| 1 | reposition patient with wedge and/or keep sacrum dry | every 10 hours | threshold < SEM delta ≤ 110% threshold |
| 2 | change mattress to pressure-alleviating mattresses | at the beginning of each nursing shift | 110% threshold < SEM delta ≤ 120% threshold |
| 3 | apply dressing over sacrum | every 12 hours | 120% threshold < SEM delta ≤ 130% threshold |
| 4 | change to dynamic mattress | every 8 hours | 130% threshold < SEM delta ≤ 140% threshold |
| 5 | apply barrier cream | every 6 hours | 140% threshold < SEM delta ≤ 150% threshold |
| 6 | apply neuro-muscular stimulation | every 4 hours | 150% threshold < SEM delta ≤ 160% threshold |
| 7 | apply topical cream to enhance perfusion | every 2 hours | 160% threshold < SEM delta ≤ 170% threshold |
| 8 | provide silicone pad under the patient's body | every 1 hour | 170% threshold < SEM delta ≤ 180% threshold |

Example 3: Identifying a Patient in Need of a Level-0 Intervention at Sacrum A patient was subjected to multiple SEM measurements at and around the boney prominence of the sacrum using an apparatus capable of measuring SEM measurements. Prior to performing the measurements, surface moisture and matter above the patient's skin surface were removed. An electrode of the apparatus was applied to the patient's skin with sufficient pressure to ensure complete contact for approximately one second to obtain each SEM measurement.

Figure 2A:
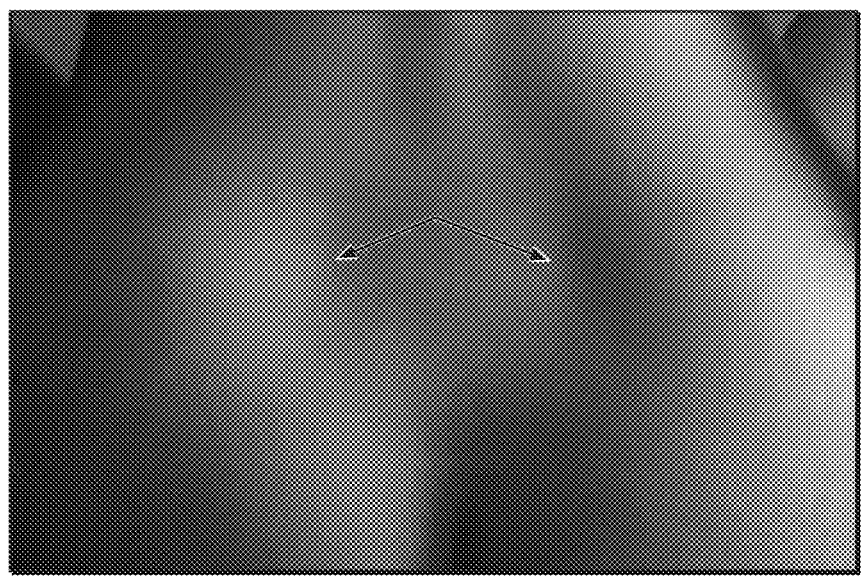
FIG. 2A is a sample visual assessment of healthy tissue in accordance with the present disclosure.
Figure 2B:
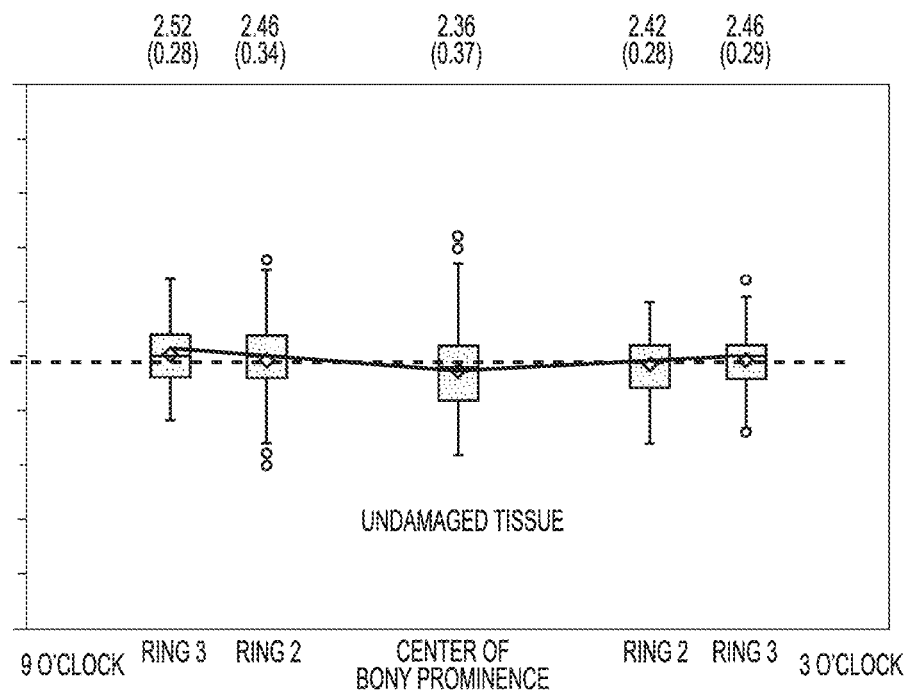
FIG. 2B is a plot of the averages of SEM measurements taken at each location at and around a healthy sacrum in accordance with the present disclosure.

SEM measurements were taken on a straight line across the sacrum of a patient. Multiple measurements were taken at a given measurement location. FIG. 2A is a sample visual assessment of healthy tissue. FIG. 2B is a corresponding plot of the averages of SEM measurements taken at each location. A threshold of 0.5 was chosen. A delta value was calculated as the difference between the maximum average SEM value and the minimum average SEM value, which was determined to be less than 0.5. Because the SEM delta value was below the threshold value, the patient was identified to be in need of a level-0 intervention. Accordingly, the patient was placed on a standard mattress, and was turned every 24 hours.

Additional SEM measurements were taken every 24 hours until discharge. There was no change in the intervention level.

Example 4: Identifying a Patient in Need of a Level-n Intervention at Sacrum A patient was subjected to multiple SEM measurements taken on a straight line across the sacrum in accordance with the same procedure as described in Example 3.

Figure 3A:
FIG. 3A is a sample visual assessment of damaged tissue in accordance with the present disclosure.
Figure 3B:
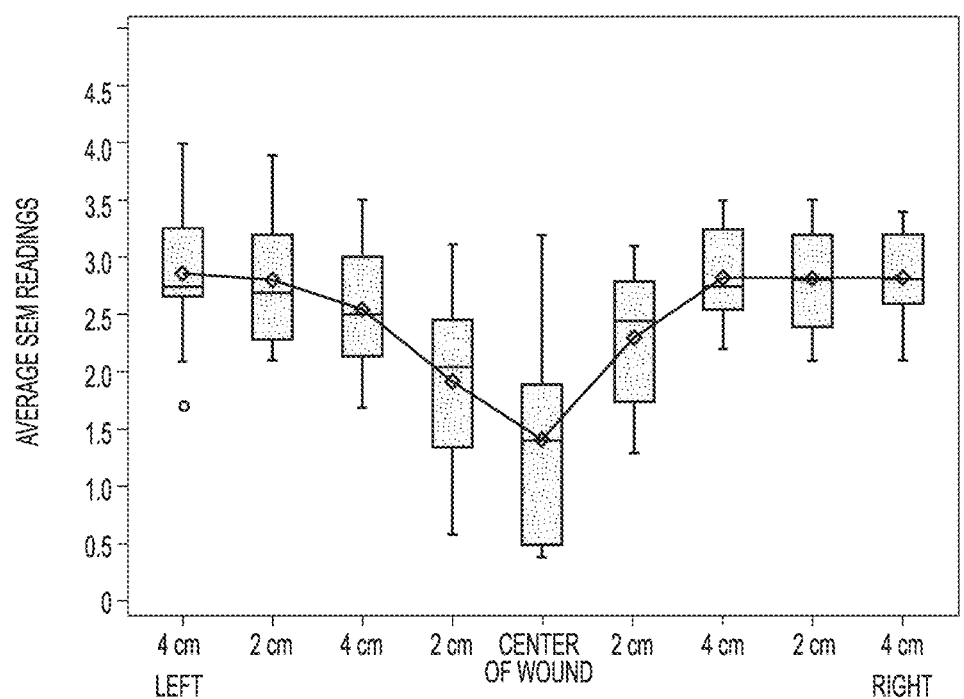
FIG. 3B is a plot of the averages of SEM measurements taken at each location at and around a damaged sacrum in accordance with the present disclosure.

FIG. 3A is a sample visual assessment of damaged tissue. FIG. 3B is a corresponding plot of the averages of SEM measurements taken at each location. A threshold of 0.5 was chosen. A delta value was calculated as the difference between the maximum average SEM value and the minimum average SEM value, which was determined to be above 0.5. Because the SEM delta value was more than 200% over the threshold value, the patient was identified to be in need of a level-8 intervention. Accordingly, the patient was placed on a silicone pad and monitored on an hourly basis until a SEM delta value of less than 170% of the threshold value was observed, at which point, the patient was switched to a level-7 intervention.

Figure 4:
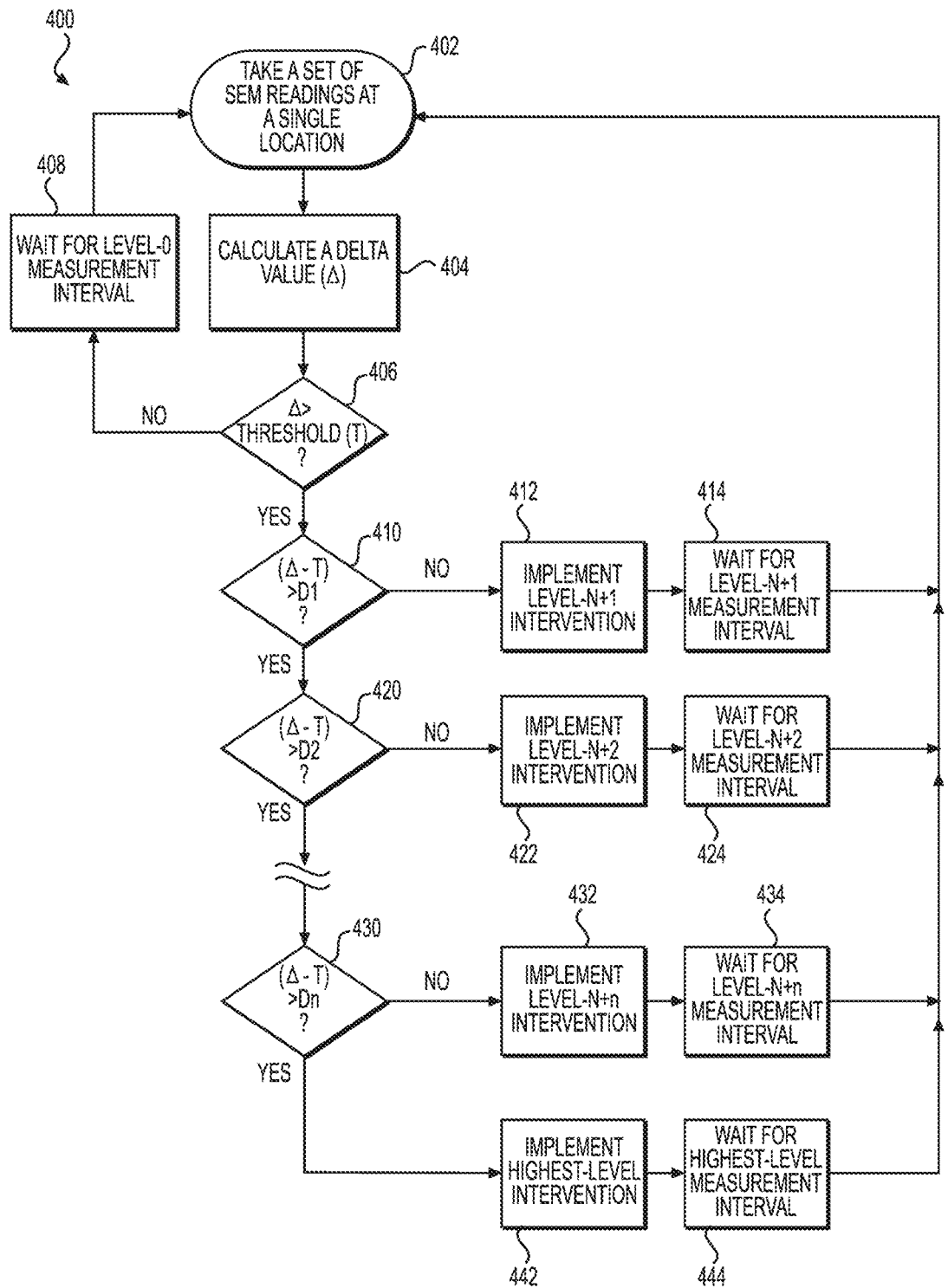
FIG. 4 is an illustration of a process for selecting a level of intervention and monitoring based on the amount by which a delta value derived from SEM measurements exceeds a threshold value in accordance with the present disclosure.

Example 5: Example Process for Selecting a Level of Intervention and Monitoring FIG. 4 is an illustration of a process 400 for selecting a level of intervention and monitoring based on the amount by which a delta value derived from SEM measurements exceeds a threshold value. Here, a caregiver took a plurality of SEM measurements at a location on the skin of a patient using a SEM Scanner in step 402, where each measurement generated a SEM value. Using a portion of these SEM values, a delta value "a" was calculated in step 404. The delta value was calculated by subtracting the smallest SEM value from the largest SEM value generated from the plurality of SEM measurements.

The calculated delta value was compared to a threshold value "T" in step 406. If the delta value was less than or equal to the threshold value, step 408 was executed and the caregiver waited until the monitoring interval associated with the current level of care transpires, then repeated the SEM measurements in step 402. If the delta value was greater than the threshold value, the amount by which the delta value exceeded the threshold value was compared to a cascading series of difference values.

In some instances, the delta value was positive and the comparison executed by subtracting the threshold value from the delta value, which produced a positive difference, and then a determination was made regarding whether the difference exceeded the first difference D1 in step 410. If the difference was less than D1, the process branched to step 412 and then step 414 to implement an intervention and measurement interval, respectively, associated with level-N+1. In this example, N had a value of zero or greater.

In some instances, the delta value was negative, for example if the SEM measurement at the center position of the data in FIG. 3B is subtracted from an average of the SEM values from the leftmost and rightmost locations in FIG. 3B. In that case, the differences D1, D2 through Dn was selected to have negative values that could have different absolute values than the corresponding difference values D1, D2 through Dn used for a positive delta value. Alternatively, the comparisons in steps 410, 420, and 430 were changed to "≤" in place of the "≥" shown in FIG. 4.

Example 6: Workflow Guidance Matrix

FIG. 5 is an example of a workflow guidance matrix 500 where the current level of intervention 502 and the new delta value 504 are used to select the new level of intervention 506. Here, a caregiver monitored the condition of a patient by periodically taking a plurality of SEM measurements at one or more locations on the patient's skin. At the time of these measurements, the patient received care associated with a level of intervention and monitoring. In this example, level-0 (zero) was associated with a patient who was not considered to be at significant risk for development of a pressure ulcer. Higher levels of intervention and monitoring were identified with the gradations of intervention ranked, for example, according to cost, difficulty to implement, or other parameter identified by the care facility. When a caregiver was making a new set of SEM measurements, they consulted this matrix by identifying the row of the current level of intervention 502, the delta value determined from the latest set of SEM measurements 504, and identified the level of intervention in the cell 506 at the intersection of the row 502 and column 504. The caregiver could consider the identified level of intervention as well as the current level of intervention and the value of the delta in selecting a level of intervention for the next time period.

In some instances, the values of the new levels of intervention in the cells 506 were similar from row to row. In some instances, the values of the new levels of intervention in adjacent cells 506 differed by a single level or by more than one level. In some instances, the values of the new levels of intervention in adjacent cells 506 were the same in adjacent cells.

Example 7: Progression of Tissue Condition Leading to Pressure Ulcer

FIGS. 6A, 6B, and 6C depict an illustrative non-limiting example of a progression over time of the tissue condition leading to a pressure ulcer. FIG. 6A depicts a cross-section of healthy tissue 600, including the stratum corneum 602 and healthy cells 604 in the epidermis/dermis. The center electrode 606 and the toroidal electrode 608 of a SEM scanner are shown in cross-section in contact with the stratum corneum 602. An illustrative indication of the sensitive region of the SEM Scanner is shown as the oval region 610. The region 610 has a depth of sensitivity. In some instances, the depth of sensitivity is in the range of 0.14 0.16 inches. In some instances, the depth of sensitivity is less than 0.16 inches.

FIG. 6B is an illustrative cross-section of slightly damaged tissue 620. Cellular damage, for example resulting from long-term application of low-level pressure has affected the tissue. Without being limited by theory, some of the cells 622 have ruptured, releasing the fluid contents into an intercellular space 624. Alternatively, and without being limited by theory, an inflammatory reaction has caused fluid to migrate into the intercellular space 624. This damage is not visible on the skin surface.

FIG. 6C is an illustrative cross-section 640 of a more advanced level of damage. Without being limited by theory, the tissue is now mostly ruptured cells 622, which can provide little mechanical structure to carry the continued applied pressure. The tissue thickness is reduced, with the bone 642 now closer to the skin surface. The ruptured cells 622 and intercellular space 624 are compressed, expelling the fluid 644 out of the local tissue as indicated by arrows 646.

Figure 6D:
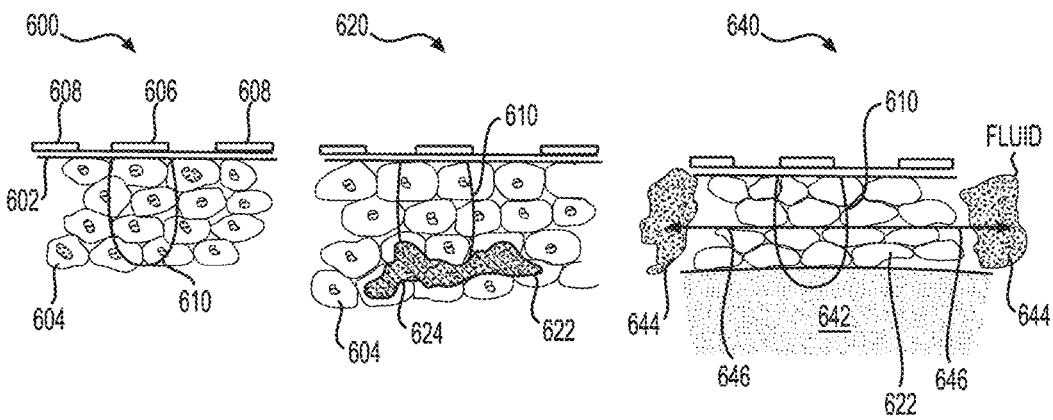
FIG. 6D is an example plot of a delta value change over time for a single patient at a single location where a pressure ulcer develops in accordance with the present disclosure.
Figure 6D:
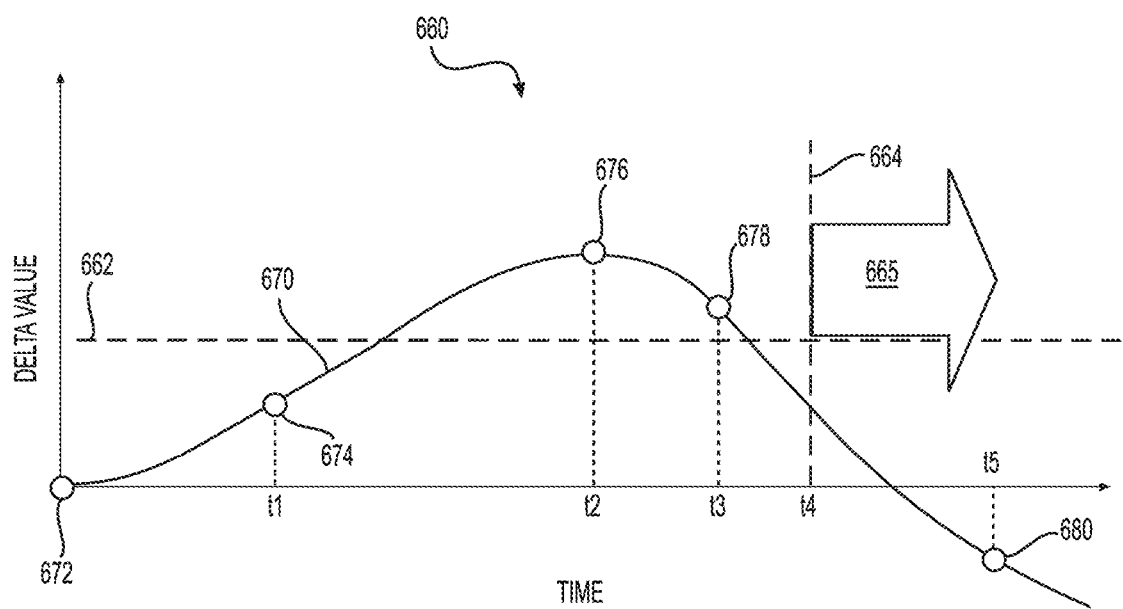

FIG. 6D shows an illustrative plot 660 of a delta value for a single patient at a single location where a pressure ulcer develops. The SEM values were measured by a SEM scanner. A delta value was generated from sets of SEM measurements taken at incremental times. Point 672 was a measurement at time=zero where all the SEM values had a baseline value associated with healthy tissue and the delta value is zero. At time t1, another set of SEM measurements was made and the associated delta value was indicated at point 674. This delta value was below the threshold 662 and, therefore, there was no indication of significant subsurface damage.

At time t2, the damage progressed and the delta value 676 was greater than the threshold 662, indicating that there was significant damage. This damage was still not visible on the skin. Nonetheless, a delta value greater than the threshold 662 indicated that there was cellular damage at a depth less than the sensitive depth of the SEM scanner.

At time t3, the damage continued but the amount of fluid in the intercellular space was decreased due to mechanical expulsion as illustrated in FIG. 6C. This reduced the SEM value taken over the damaged area, which reduced the computed delta value 678 since the SEM value of the healthy tissue remained much the same as during previous measurements.

At time t4, the damage progressed to the point where it was visible on the skin surface, as shown in FIG. 3A. In some instances, time t4 may occur before one or both of t2 and t3. In some instances, time t4 may occur after the delta value has reached zero again along curve 670 after time t3 and before t5. Arrow 665 indicates that after time t4, the damage remained visible. In some instances, the tissue may be considered to be a "stage 1" pressure ulcer after time t4.

At time t5, the damage progressed to the point where sufficient fluid had been expelled from the local tissue that the SEM value of a measurement made over the damaged area was lower than the SEM value of healthy tissue. This resulted in the delta value 680 being negative, as shown in FIG. 3B. In some instances, the negative delta would indicate that the tissue is seriously damaged. In some instances, the negative delta would indicate that a portion of the tissue at the location of the lowest SEM value is necrotic.

Example 8: Method of Mapping an Area of Possible Damage I

Figure 7A:
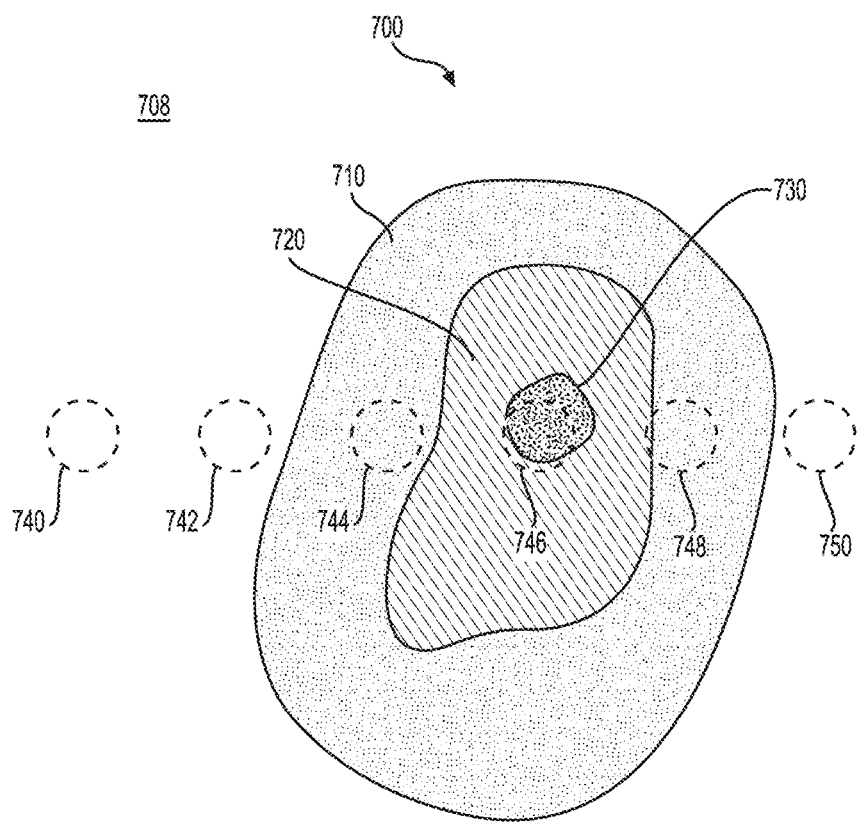
FIGS. 7A and 7B are examples of methods of mapping areas of tissue damage in accordance with the present disclosure.

FIG. 7A is an example of a method of mapping an area of possible damage. The area of damage 700 was surrounded by healthy tissue 708. The center area 730 was significantly damaged. The first surrounding area 720 was less damaged, and the second surrounding area 710 was less damaged but still not healthy tissue. The skin over all of these areas had the same appearance and texture, with no indication of the subsurface damage. The series of dashed-line circles 740, 742, 744, 746, 748, and 750 indicate an example set of location where SEM measurements were taken. SEM measurements taken at locations 740, 742, and 750 generally produced a SEM value associated with healthy tissue, identified within this example as "H." SEM measurements taken at locations 744 and 748 generally produced a SEM value "J" that is slightly higher than H. A SEM measurement taken at location 746 generally produced a SEM value "P" that is greater than J. All of these measurements were considered to be taken at a single "location" on the patient's body, for example the sacrum, even though the individual locations were spatially dispersed over this location. For this set of SEM values, the delta was the difference between the highest SEM value, which likely occurred at location 746, and the lowest SEM value, which likely occurred at one of locations 740, 742, and 750, within this set. If the delta was greater than a threshold value "T," this was an indication that there is significant damage at this location. The exact location of the greatest damage was likely to be proximate to the measurement location 746 where the greatest SEM value was produced.

Example 9: Method of Mapping an Area of Possible Damage II

Figure 7B:
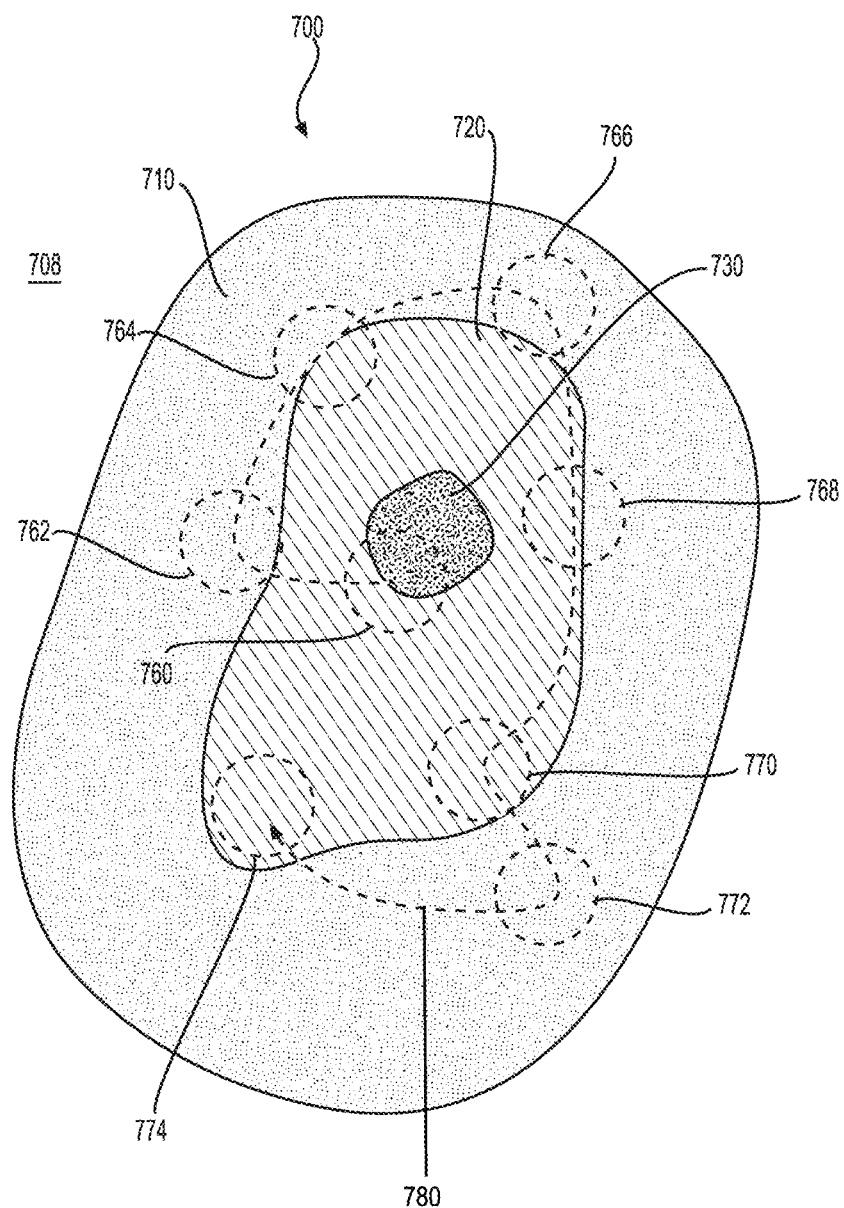

FIG. 7B depicts a second example of mapping an area of possible damage. In this example, the approximate location of the greatest damage was known, for example from prior application of the method illustrated in FIG. 7A. The intent of this method was to map the boundary between area 710 and area 720 to determine the extent of the damage. For simplicity, the SEM values produced by measurements in each area were the same and the SEM values increased from area 710 to area 720 and then to area 730. The first SEM measurement was taken at location 760, which was known to be the approximate location of the greatest damage. Subsequent measurements were taken at locations 762, 764, 766, and 768 in the order indicated by path 780. The SEM value produced at location 764 was slightly higher than the SEM values produced at locations 762 and 766, indicating that location 764 was partially within the area 720 while locations 762 and 766 were fully within the lesser-damaged area 710. The boundary could be approximated by interpolating between the various measurement locations. For example, the SEM value produced at location 770 was high enough to suggest that it is fully within the area 720 and therefore did not help identify the boundary between areas 710 and 720. The subsequent location 772 was therefore directly away from the starting location 760. As location 760, in this example, was now fully within area 710, the boundary between areas 710 and 720 could be interpolated to be between locations 770 and 772. The SEM value produced from a measurement at location 774 was similar to the SEM value from location 770 and it could be sufficient to identify the boundary as outside the location 774 without taking another measurement at a location corresponding to location 772.

This set of measurements enabled the creation of a map of a certain level of damage, for example the area 720. Repeating this mapping process at regular time intervals would provide an indication of whether the area 720 is growing, which may indicate that an increased level of intervention is appropriate, or shrinking, which may indicate that the current level of intervention is allowing the damage to heal.

Example 10: Treatment Decision Pathway for Stratifying Patients and Providing Appropriate Treatments FIG. 8A outlines a currently recommended treatment decision pathway for preventing pressure ulcers in hospital patients as presented by The National Institute for Health and Care Excellence (NICE) in their clinical guideline *Pressure ulcers: prevention and management*, published 23 Apr. 2014. The guidelines recommend that a risk analysis be performed for every patient admitted to a care facility that exhibits one or more risk factors such as significantly limited mobility, a significant loss of sensation, a previous or current pressure ulcer, a nutritional deficiency, an inability to reposition themselves, or a significant cognitive impairment. Risk assessment is commonly done using a scored checklist, such as the Braden Scale, that assesses the severity of specific risk factors.

Upon completion of the risk assessment, the patient is identified as (i) having a low risk of developing a pressure ulcer, (ii) being at risk of developing a pressure ulcer, or (iii) being at high risk of developing a pressure ulcer. Depending on the level of risk the patient is classified as having, the patient undergoes different sequences of treatment and evaluation by visual assessment.

All patients are potentially at risk of developing a pressure ulcer. They are more likely to occur in people who are seriously ill or have a neurological condition, impaired mobility, impaired nutrition, poor posture, or a deformity.

Pressure ulcers are categorized as stage-1 through stage-4, with stage-1 being the lowest condition. The National Pressure Ulcer Advisory Panel (NPUAP) has defined a "stage-1" ulcer as intact skin with a localized area of non-blanchable erythema, where "blanchable" indicates that the tissue loses all redness when pressed and "non-blanchable" tissue remains red when pressed due to the presence of red blood cells outside of blood vessels (extravasation). In some patients, blanchable erythema or changes in sensation, temperature, or firmness may precede visual changes.

Visual skin assessment (VSA) is the current method of identifying a pressure ulcer. A trained healthcare professional assesses the appearance of the skin, visually and tactilely, looking for redness or variations in tissue firmness, tissue temperature, or moisture.

If a patient is identified as having a low risk of developing a pressure ulcer, the patient is simply monitored for a change in clinical status such as undergoing surgery, worsening of an underlying condition, or a change in mobility. A patient who uses a wheelchair or sits for prolonged periods may be provided with a high-specification foam cushion or equivalent pressure-distributing cushion. If there is no change in clinical status, a low-risk patient will not be reassessed under this set of guidelines and stays within the same treatment and evaluation pathway until he or she is discharged from the care facility.

If a patient is identified as being at risk of developing a pressure ulcer, the patient will be scheduled to be turned, or "rounded," every 6 hours. As with the low-risk patient, a high-spec foam cushion may be provided if the patient uses a wheelchair or sits for prolonged periods of time. No other monitoring or intervention is recommended by the NICE guidelines.

A high-risk patient receives a high-spec foam mattress as a preventative measure, provided with a high-spec cushion if they are in a wheelchair or sit for prolonged periods of time, and will be turned every 4 hours. The patient will receive a daily VSA for all areas of the body. If an area is found to have non-blanchable erythema, an appropriate intervention will be implemented and that area re-checked by VSA every 2 hours. Areas that do not exhibit non-blanchable erythema are re-checked daily by VSA. A personalized care plan will be developed for each high-risk patient.

It can be seen from this flow chart that the majority of the time spent by caregivers will be on the high-risk patients. While this may be appropriate, it leaves the at-risk patients unmonitored and they may develop a stage-1 ulcer before the condition is observed by a caregiver. Furthermore, the consequence of relying on VSA to detect a problem necessarily means that patients will develop a stage-1 ulcer before an intervention is selected or implemented. By the time that the damage has progressed to stage-1, it is likely that the skin will break and become a stage-2 ulcer despite intervention. There is a clear need to identify tissue damage earlier so that interventions can prevent progression of the subepidermal damage to stage-1 and beyond.

Figure 8A:
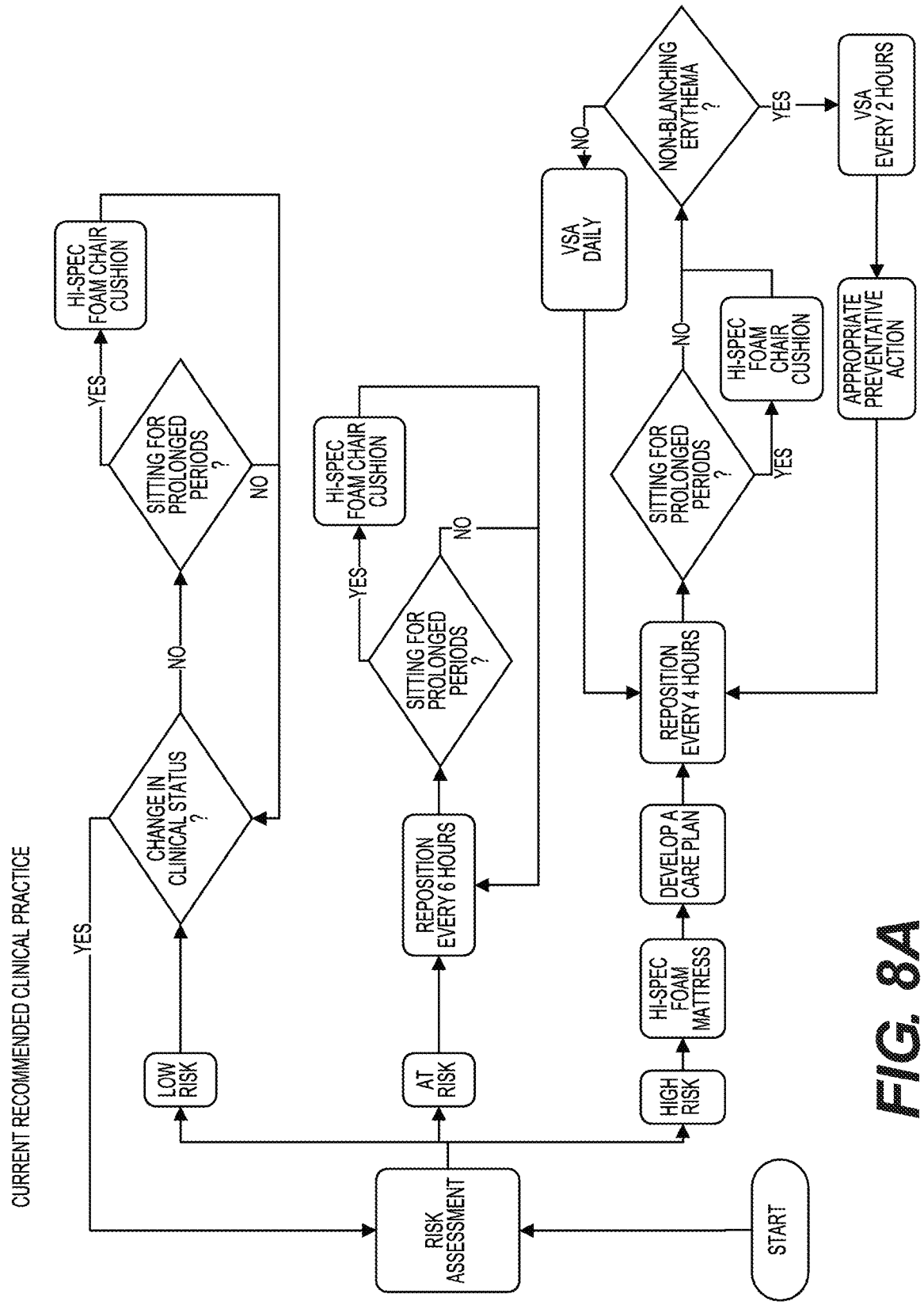
FIG. 8A is an example of a currently recommended treatment decision pathway for preventing pressure ulcers in hospital patients using a combination of risk assessment and visual assessment.
Figure 8B:
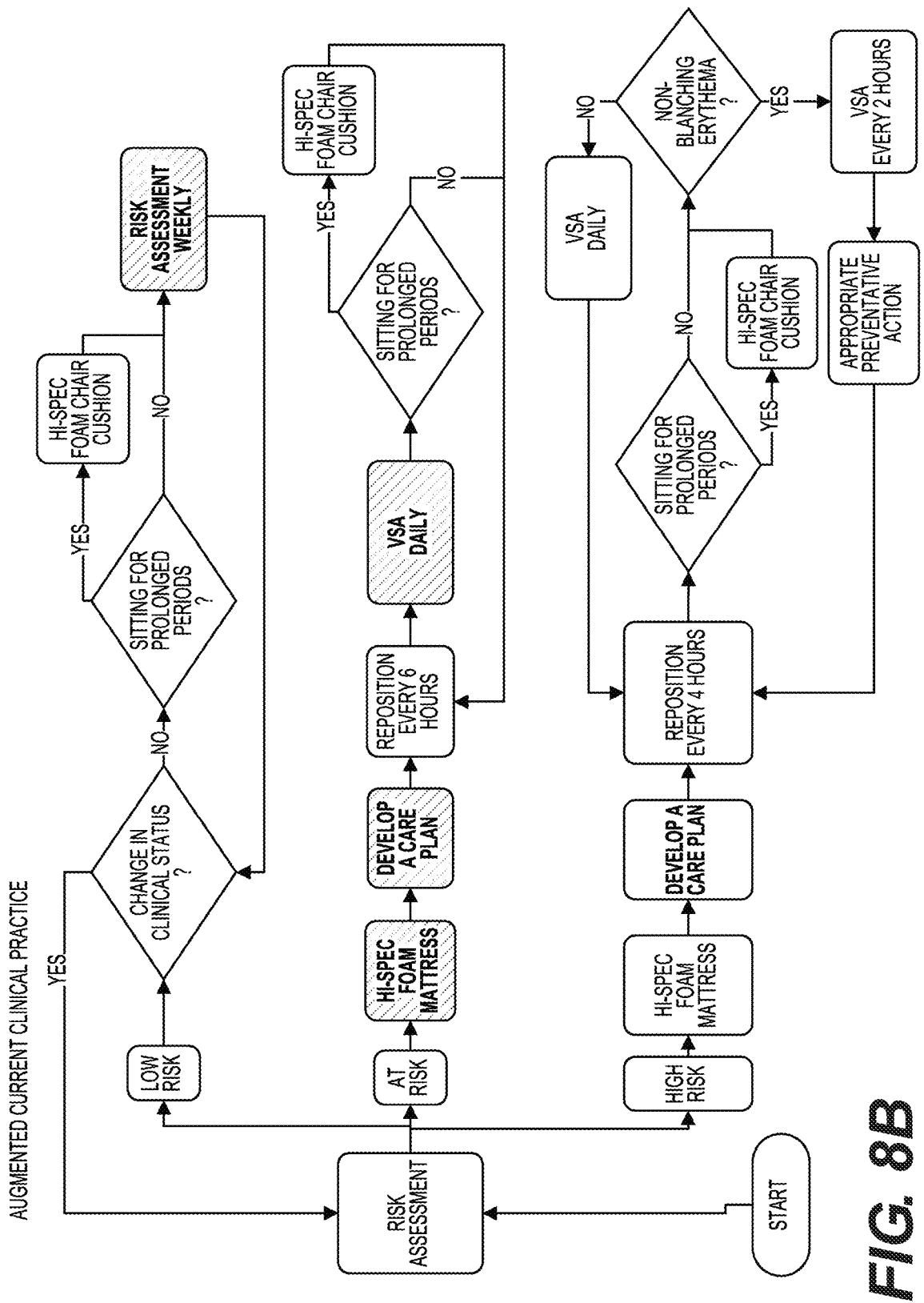
FIG. 8B is an example of a current augmented treatment decision pathway for preventing pressure ulcers as currently implemented at some health care facilities.

FIG. 8B is an example of a current augmented treatment decision pathway for preventing pressure ulcers as currently implemented at some health care facilities. The augmented pathway adds monitoring steps to both the at-risk and the low-risk paths. A low-risk patient received a weekly risk assessment, for example completion of the Braden Scale assessment. A patient identified as at-risk in the initial assessment will receive a high-spec foam mattress as a preventative measure and will be evaluated daily by VSA. A care plan will be developed for the monitoring and treatment of the at-risk patient. No change is made in the care if a high-risk patient.

The augmented plan has the benefit of providing basic monitoring of all patients for pressure ulcers. The additional steps require additional time, however, either by adding staff or further burdening the existing staff. While superior to the recommended care pathway of FIG. 8A, the care pathway of FIG. 8B requires more resources and still suffers from the limitation that a patient must develop a stage-1 ulcer before VSA identifies the damage.

Various hospitals and care facilities use different numbers of risk categories, ranging from two categories, low-risk and at-risk, to four or more categories, adding categories such as "very-high-risk" to the categories of the example of FIG. 8B. Patients are assigned to the various categories based on the results of the initial risk assessment.

Figure 9:
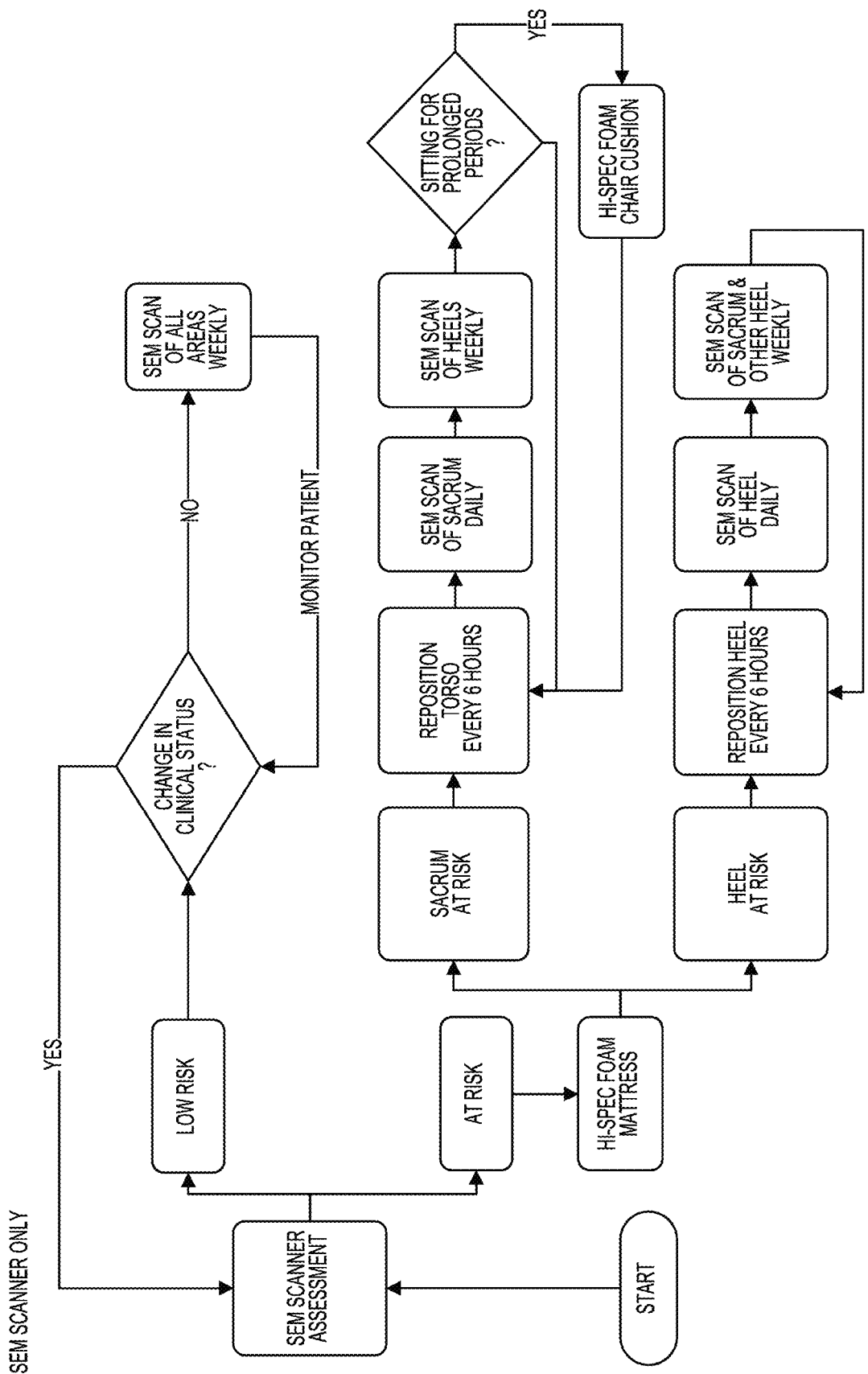
FIG. 9 is an example flowchart of how a SEM Scanner may be used in a stand-alone process to prevent pressure ulcers, in accordance with the present disclosure.

FIG. 9 is an example flowchart of how a SEM Scanner may be used in a stand-alone process to prevent pressure ulcers, in accordance with the present disclosure. Every incoming patient receives a complete SEM scanner assessment of all body locations that are selected for monitoring. These selected locations may include areas recommended in the Instructions For Use (IFU) of the SEM scanner, such as the sacrum and the heels. Additional locations may be identified by the hospital and integrated into their in-house practice. Multiple SEM measurements are taken at and around each body location at positions that are separated from each other, although this is generally referred to as taking multiple measurements at the body location. The SEM scanner calculates a "delta" value for each location from the set of measurements taken at and around that location. The delta value is then compared to one or more threshold values to categorize a patient. In this example, the patient is assigned to one of two risk categories: low-risk and at-risk.

In an aspect, the clinician will perform an SEM scan of a body location identified as having possible damage in the initial SEM scan at a first time interval. The clinician will also perform an SEM scan of all other body locations selected for monitoring at a second time interval that is longer than the first time interval. In an aspect, the values of the first and second time intervals are different depending on the risk category to which the patient has been assigned. For example, a high-risk patient will have a first time interval of 4 hours and a second time interval of 1 day while an at-risk patient will have a first time interval of 1 day and a second time interval of 1 week. In an aspect, the time interval may be event-based, for example upon a change of attending staff or shift change, rather than strictly based on time. In general, body locations that have elevated delta values are scanned more often than other body locations that are monitored but having normal delta values in previous SEM scans.

In an aspect, the interval at which an SEM scan is performed is determined by the delta values from the prior SEM scan. For example, an SEM scan of a body location that had a delta value greater than or equal to a first threshold in a previous SEM scan is performed at a first time interval, while an SEM scan is performed at a second time interval that is shorter than the first time interval when the prior SEM scan of a body location had a delta value greater than or equal to a second threshold that is higher than the first threshold.

In this example, low-risk patients receive a weekly SEM scan of all body locations that are selected for monitoring. This is a small effort that provides basic protection for even the healthiest patients, as a weekly SEM scan is likely to detect tissue damage before it becomes visible to VSA.

At-risk patients, which will include patients that would be identified as high-risk in the current care pathways of FIGS. 8A and 8B, will receive specialized care based on the body location that exhibits a delta value above a threshold. For example, if the sacrum body location has a delta value above a threshold, the patient will be repositioned every 6 hours and receive a SEM scan of the sacrum every day and an SEM scan of the other body locations every week.

Figure 10:
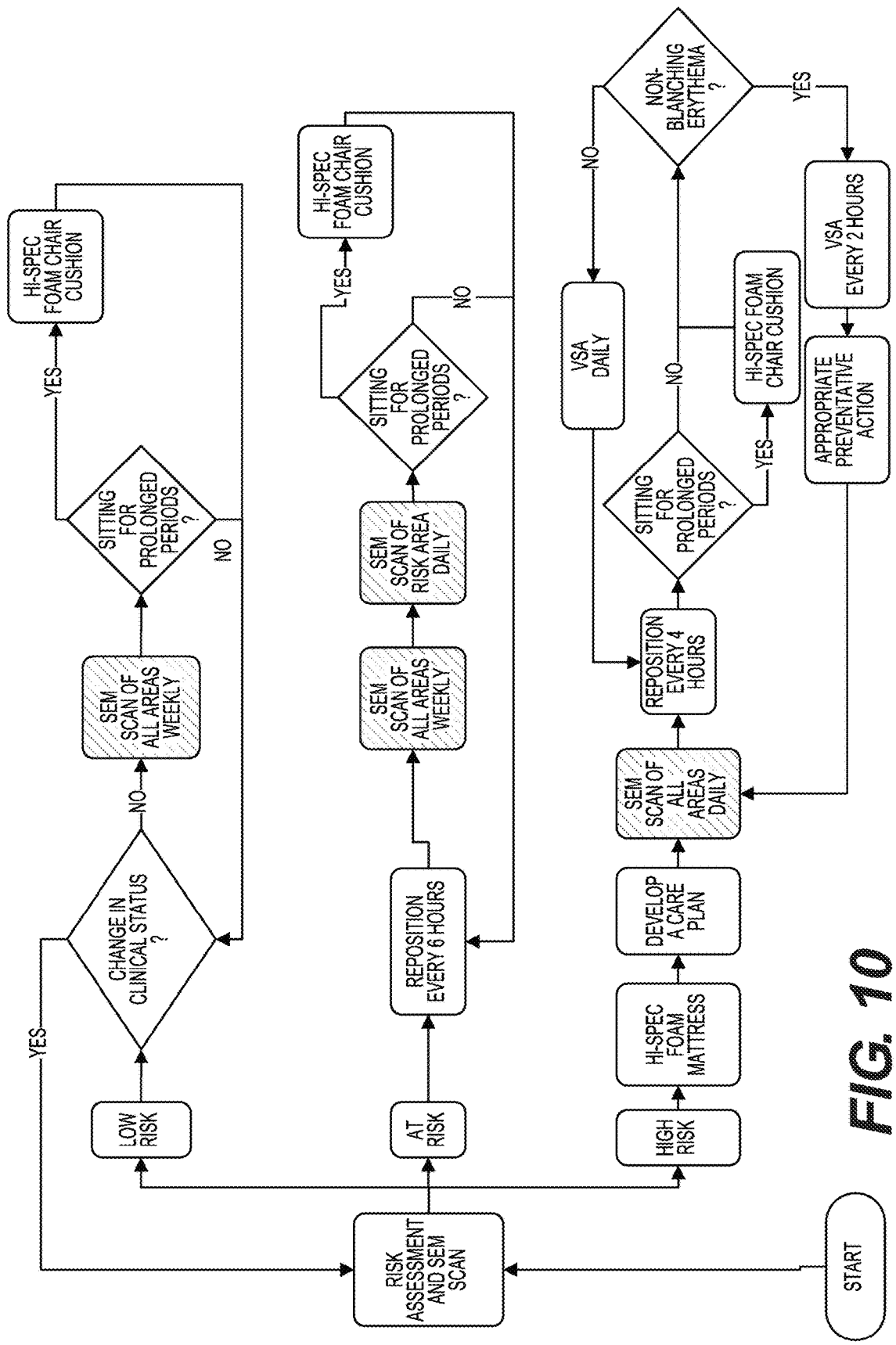
FIG. 10 is an example flowchart of how a SEM Scanner may be used as an adjunct to further improve the augmented treatment decision pathway of FIG. 8B, in accordance with the present disclosure.

FIG. 10 is an example flowchart of how a SEM Scanner may be used as an adjunct to further improve the augmented treatment decision pathway of FIG. 8B, in accordance with the present disclosure. An incoming patient receives both a risk assessment and an SEM scan of all body locations identified by the hospital for monitoring and the assignment of a patient to a risk category is based partially on the risk assessment and partially on the SEM scan results. An initial delta value that is greater than a threshold is an indication that there is possible damage at that body location. In an aspect, the assignment is based solely on the largest initial delta value found during the initial SEM scan.

A decision whether to implement an intervention, for example turning the patient at a first interval, is currently based on the VSA and risk assessment despite the uncertainty of whether there is early stage damage below the skin. In an aspect, the decision to implement an intervention for a particular body site, or a general intervention such as a high-spec mattress, is based on the delta value found for that site in the SEM scan. If the delta value is less than a predetermined threshold, no intervention is required. If the delta value is greater than the predetermined threshold, then an intervention is selected and implemented based partially on the body location and partially on the delta value for that body location. The predetermined threshold for whether or not to select and implement an intervention may be higher or lower than the threshold for determination that there is possible damage at the body location.

A comparison of the costs of provided the care pathways of FIGS. 8A, 8B, 9, and 10 reveals one of the benefits of utilizing the SEM scanner to monitor patients. Note that the costs cited herein are for patients who do not have or develop pressure ulcers, in which case the estimated treatment cost jumps to $2000 for a stage-1 ulcer.

The baseline for this comparison is the augmented current practice of FIG. 8B, which represents a current "best practice" for hospitals striving to reduce the incidence rate of pressure ulcers. Providing the care of the low-risk care pathway is expected to cost an average of $26 per patient for the average hospital stay of 5.6 days, the care for an at-risk patient is estimated to cost an average of $121, and a high-risk patient is expected to cost $165. All of the care pathways rely on a VSA to detect a pressure ulcer and are otherwise implementing interventions based on "typical" patient progression rather than the particular patient's condition.

Integrating the SEM scanner into the current "best practice" workflow, as shown in FIG. 10, does not lower the cost of any of the care pathways as no work element is being eliminated. The benefit is in the ability to detect tissue damage at an earlier stage at a minimal incremental cost. The incremental cost of adding a SEM scan to the no-risk care pathway is $2, raising the cost from approximately $26 to $28. The expected cost of caring for an at-risk patient who does not have an elevated SEM scan delta value, i.e. does not have subepidermal tissue damage, is also increased by only $2. If an at-risk patient is found to have an elevated SEM scan delta value, however, the patient is escalated to the high-risk category, where the expected cost of care increases from $165 to $169. While this may seem like an additional cost at first glance, it represents an increase in the level of protection provided to at-risk patients.

FIG. 9 represents an example workflow that relies solely on an SEM scanner to monitor patients and forgoes the routine VSA. The expected cost of preventative care for a low-risk patient is $4, compared to the $28 cost for the integrated low-risk care pathway of FIG. 10. For an at-risk patient, which is the only other category for the SEM scanner care pathway of FIG. 9, the expected cost is $97, compared to the $123-$169 costs for the at-risk and high-risk patients of the integrated care pathway of FIG. 10.

Figure 11:
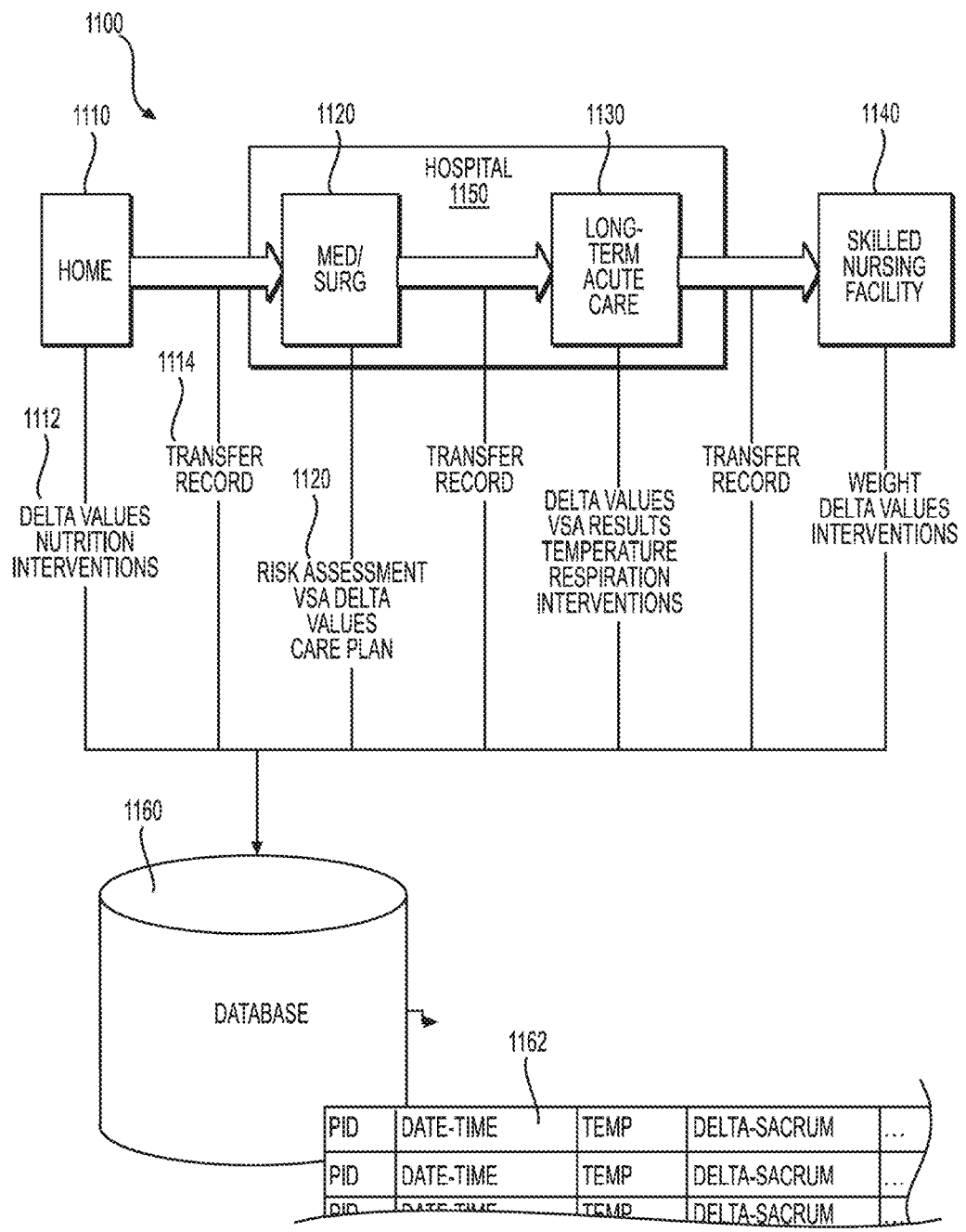
FIG. 11 illustrates the concept of providing a continuity of care across multiple care settings, in accordance with the present disclosure.

FIG. 11 illustrates the concept of providing a continuity of care across multiple care settings, in accordance with the present disclosure. This example shows a care pathway 1100 for a patient being sequentially cared for in a plurality of care settings, starting from a home care setting 1110. A decision is made to transfer the patient to a hospital 1150 where the patient is initially admitted to a medical/surgical (med/surg) unit 1120. After receiving care in the med/surg unit 1120 for some time, the patient is transferred to a long-term care unit 1130 within the same hospital 1150. After further treatment, the patient is discharged from the hospital 1150 to a skilled nursing facility 1140. Although not shown in FIG. 11, care pathway 1100 is not limited to this sample sequence and combination of care settings. For example, care pathway 1100 may also involve a discharge of a patient back to the home care setting.

In an aspect, a central "registry" or database 1160 is established to aggregate data from all care settings as well as the condition of the patient at the time of transfer between care settings.

While in each care setting, for example the home care setting 1120, health information regarding the patient is recorded and transferred to the database 1160 in a data record 1112. The health information may include the results of examinations or tests, observations, measurements, treatments, the implementation of interventions that are intended to prevent the development of pressure ulcers, dietary notations, and other records related to the condition and treatment of the patient. A data record from a care setting may include one or more of a patient identifier, a data element from the group of nutritional information, an implemented intervention, a risk assessment, a visual skin assessment, a care plan, a doctor's note, lean event, a vital sign, a "measure of health" such as skin redness or an indication of mobility or a measure of cognition, a body weight, and a lab result, and a date/time associated with the data element. Data records may vary in structure and content. A data record reported to the database may contain one of more of the following data elements:

a) a patient identifier
b) a transaction date
c) a facility identifier d) a location of the transaction
e) nutritional information
f) an implemented intervention
g) a risk assessment
h) a visual skin assessment
i) a care plan
j) a doctor's note (diagnosis, order, prescription, request for test, procedure, treatment, etc.)
k) results of a test, procedure, or treatment
l) an event
m) a vital sign
n) a body weight
o) a lab result When a patient is transferred between care setting, for example from the home care setting 1110 to the med/surg care setting 1120, a transfer record 1114 is created and reported to the database 1160. Transferring information regarding risk and health information related to pressure ulcers will improve the care provided in the new care setting. In an aspect, the transfer record 1114 comprises a patient assessment performed at the "from" care site after the decision to transfer the patient has been made. In an aspect, the assessment comprises an SEM scan of at least one body location, wherein the SEM scan comprises a plurality of SEM values measured at a single body location and calculation of a delta value from the plurality of SEM values. In an aspect, the transfer record contains a history of prior SEM values and/or delta values while in the "from" care setting. In an aspect, the transfer record contains one or more of a VSA, a risk analysis, and other health data. A transfer record may contain one of more of the following data elements:

a) a patient identifier
b) a transaction date/time (date and time, time zone or Greenwich Mean Time)
c) a transaction type (pre-admit, admit, transfer, discharge, etc.)
d) a "To" Location
e) a "From" Location
f) a facility/unit identifier
g) a risk assessment
h) a visual skin assessment
i) a photograph of a body location A patient may move periodically from a primary care setting, for example a home care setting 1110, to an advanced care setting, for example a long-term acute care unit 1130, where the patient will undergo an "episode of care" by doctors or other skilled professionals. Data records of the assessments and care provided in the advanced care setting are reported to the database 1160. Upon discharge from the long-term acute care setting 1130 to the home setting 1110, data records containing care instructions, prescriptions, and other guidance for care in the home setting 1110.

With data from the entire care pathway 1100 aggregated in the database 1160, it is possible to query the database 1160 to retrieve the delta values observed over time for a particular patient across multiple care settings and various episodes of care.

In an aspect, a query is structured to determine whether instructions from monitoring and/or treatment of a patient are being followed.

In an aspect, a query is structured to determine whether a treatment of a patient is effective.

In an aspect, a query is structured to determine whether an outcome of a patient is related to one or more of the data elements reported to the database 1160.

In an aspect, a query is structured to retrieve one or more measures of health along with delta values to evaluate possible linkages between the retrieved measures of health and the development of a pressure ulcer or other outcomes (development of other health con. The delta values are plotted against the date/time of measurement to form a time history of the delta values for a body location. In an aspect, the dealt values are analyzed to determine one or more of a slope, an acceleration, a curve shape and associated characteristics, and a time-to-intercept of a selected threshold value. In an aspect, these analytical results can be used to implement the methods and processes of FIGS. 1 and 4.

From the foregoing, it will be appreciated that the present disclosure can be embodied in various ways, which include but are not limited to the following:

While the present disclosure has been described with reference to particular aspects, it will be understood by those skilled in the art that various changes may be made and equivalents may be substituted for elements thereof without departing from the scope of the disclosure. In addition, many modifications may be made to a particular situation or material to the teachings of the disclosure without departing from the scope of the disclosure. Therefore, it is intended that the disclosure not be limited to the particular aspects disclosed but that the disclosure will include all aspects falling within the scope and spirit of the appended claims.

I claim:

1. A method of providing a continuity of care for a patient at risk of developing pressure ulcers (PU) during transfer from a first care setting to a second care setting, the method comprising the steps of:

identifying a current PU intervention of level-K received by the patient at the first care setting, wherein the current PU intervention of level-K is provided in a transfer record, wherein the transfer record further comprises results obtained from performing a first SEM scan of at least one body location of the patient while in the first care setting, wherein the first SEM scan comprises a plurality of measurements of an SEM value at the body location and calculation of a first delta value from the plurality of SEM values, wherein if the current PU intervention of level-K is a level-0 PU intervention, the level-0 PU intervention comprises performing a daily SEM scan of at least one body location of the patient;

making a plurality of Sub-Epidermal Moisture (SEM) measurements at a body location on the patient at the second care setting, each SEM measurement comprising a measurement of biocapacitance, calculating a delta value by a difference between a maximum SEM value and a minimum SEM value of the plurality of SEM measurements, determining whether the delta value exceeds a threshold, making a further plurality of SEM measurements at a pre-determined frequency corresponding to level-K if the delta value does not exceed the threshold, wherein the pre-determined frequency corresponding to level-K is longer than every 15 minutes and if the delta value does not exceed the threshold, continuing to administer the current PU intervention of level-K based on the delta value, wherein level-K corresponds to a risk level for pressure ulcer, or making the further plurality of SEM measurements at a pre-determined frequency corresponding to level-N if the delta value exceeds the threshold, where N has a value greater than K, wherein the pre-determined frequency corresponding to level-N is shorter than the pre-determined frequency corresponding to level-K and longer than or equal to every 15 minutes, and administering a new PU intervention of level-N based on the delta value, wherein level-N corresponds to a higher risk level for pressure ulcer than level-K.

2. The method of claim 1, wherein the transfer record further comprises delta values calculated from a portion of the plurality of SEM scans of the patient taken at different times while in the first care setting.

3. The method of claim 1, wherein the transfer record further comprises results obtained from at least one assessment selected from the group consisting of a risk assessment of the patient, a visual skin assessment of at least one body location of the patient, and an image of the at least one body location.

4. The method of claim 1, wherein the transfer record is stored on a database.

5. The method of claim 4, wherein:
the transfer record further comprises a patient identifier and a date and a time when said first SEM scan was performed.

6. The method of claim 5, further comprising the steps of:
performing a second SEM scan of the body location of the patient in the second care setting to obtain a second plurality of SEM measurements,
calculating a second delta value,
creating a second data record that comprises the patient identifier, the second delta value, and a second date and time when the second SEM scan was performed, and
reporting the second data record to the database.

7. The method of claim 6, further comprising the step of:
querying the database for the delta value and the second delta value of the at least one body location of the patient in the transfer record and the second data record respectively to form retrieved delta values.

8. The method of claim 7, further comprising the steps of:
formatting the retrieved delta values in date and time order, and displaying the formatted delta values.

9. The method of claim 6, further comprising the steps of:
creating an additional data record that comprises the patient identifier, a data element, and a date/time associated with the data element, wherein the data element comprises one or more of a nutritional information, an implemented intervention, a risk assessment, a visual skin assessment, a care plan, a doctor's note, an event, a vital sign, a body weight, and a lab result, and
reporting the additional data record to the database.

10. The method of claim 8, wherein the formatted delta values are displayed in the form of a curve.

11. The method of claim 8, further comprising the step of analyzing the retrieved delta values to determine one or more of a slope, an acceleration, a curve shape and associated characteristics, and a time-to-intercept of a selected threshold value.

12. The method of claim 11, wherein the acceleration is determined by the rate of change of the slope of the curve.

13. The method of claim 6, further comprising the steps of:
performing a third SEM scan of the at least one body location of the patient in the second care setting to obtain a third plurality of SEM measurements,
calculating a third delta value,
creating a third data record that comprises the patient identifier, the third delta value, and a third date and time when the third SEM scan was performed, and
reporting the third data record to a database.

14. The method of claim 13, further comprising the step of
querying the database to retrieve the delta values observed over time for a particular patient across multiple care settings and various episodes of care.

15. The method of claim 1, wherein the level-0 PU intervention further comprises an intervention selected from the group consisting of providing good nutrition, standard mattress, turning every 24 hours, and a combination thereof.

16. The method of claim 1, wherein a level-1 PU intervention is providing a heel boot to the patient.

17. The method of claim 1, wherein a level-2 PU intervention is changing the patient's support surface.

18. The method of claim 1, wherein a level-3 PU intervention is applying dressing to the back or sides of the patient's heel.

19. The method of claim 1, wherein a level-4 PU intervention is changing the patient's sheet cover to a low-friction sheet cover.

20. The method of claim 1, wherein a level-5 PU intervention is providing a low-friction padded mattress surface for the patient's lower leg.

21. The method of claim 1, wherein a level-6 PU intervention is turning the patient at a shorter interval than currently provided for.

22. The method of claim 1, wherein a level-7 PU intervention is applying a barrier cream to the patient's heel.

23. The method of claim 1, wherein a level-8 PU intervention is applying a neuro-muscular stimulation to the patient's heel.

24. The method of claim 1, wherein a level-9 PU intervention is applying a topical cream to the patient's heel to enhance perfusion.

25. The method of claim 1, wherein a level-10 PU intervention is providing a silicon pad for the patient's lower leg.

* * * * *